US012767717B2

(12) United States Patent
Yeh et al.

(10) Patent No.: US 12,767,717 B2
(45) Date of Patent: Oct. 20, 2026

(54) ANTI-HUMAN PD-L1 ANTIBODIES AND THEIR USES

(71) Applicant: DEVELOPMENT CENTER FOR BIOTECHNOLOGY, New Taipei City (TW)

(72) Inventors: Shu-Ping Yeh, Taipei City (TW); Cheng-Chou Yu, Taipei City (TW); Yu-Hsun Lo, Taipei City (TW); Jin-Yu Wang, Taipei City (TW); Mei-Chi Chan, Taipei City (TW); Chao-Yang Huang, Taipei City (TW); Szu-Liang Lai, Taipei City (TW)

(73) Assignee: DEVELOPMENT CENTER FOR BIOTECHNOLOGY, New Taipei City (TW)

( * ) Notice: Subject to any disclaimer, the term of this patent is extended or adjusted under 35 U.S.C. 154(b) by 545 days.

(21) Appl. No.: 18/522,809

(22) Filed: Nov. 29, 2023

(65) Prior Publication Data

US 2024/0209095 A1 Jun. 27, 2024

Related U.S. Application Data

(60) Provisional application No. 63/428,802, filed on Nov. 30, 2022.

(51) Int. Cl.

*C07K 16/28* (2006.01)
*A61K 39/00* (2006.01)
*A61K 45/06* (2006.01)
*A61K 47/68* (2017.01)
*A61P 35/00* (2006.01)

(52) U.S. Cl.

CPC .......... *C07K 16/2827* (2013.01); *A61K 45/06* (2013.01); *A61K 47/6849* (2017.08); *A61P 35/00* (2018.01); *A61K 2039/505* (2013.01); *C07K 2317/24* (2013.01); *C07K 2317/565* (2013.01)

(58) Field of Classification Search

CPC ............ C07K 16/2827; C07K 2317/24; C07K 2317/565; C07K 2317/76; C07K 2317/92; A61K 45/06; A61K 47/6849; A61K 2039/505; A61P 35/00

See application file for complete search history.

(56) References Cited

U.S. PATENT DOCUMENTS

| | | | |
|---|---|---|---|
| 9,205,148 B2 * | 12/2015 | Langermann ........... | A61P 31/00 |
| 2016/0311903 A1 | 10/2016 | West et al. | |

FOREIGN PATENT DOCUMENTS

| | | |
|---|---|---|
| CN | 110903391 A1 | 3/2020 |
| CN | 114341180 A | 4/2022 |
| TW | 202005983 A | 2/2020 |
| WO | 2020/018395 A1 | 1/2020 |
| WO | 2021/088904 A1 | 5/2021 |
| WO | 2021/170082 A1 | 9/2021 |
| WO | 2022/147108 A1 | 7/2022 |

OTHER PUBLICATIONS

ISR for International Application PCT/US2023/081653 dated Jun. 10, 2024.

Written Opinion for International Application PCT/US2023/081653 dated Jun. 10, 2024.

Supplementary European Search Report for copending Application 23898828.1 issued on Feb. 19, 2026.

David Prihoda, et al.: "BioPhi: A platform for antibody design, humanization, and humanness evaluation based on natural antibody repertoires and deep learning", MABS, vol. 14, No. 1, Feb. 8, 2022 (Feb. 8, 2022).

Stuart Rudikoff, et al.: "Single amino acid substitution altering antigen-binding specificity", Proceedings of the National Academy of Sciences (PNAS), National Academy of Sciences, vol. 79, No. 6, Mar. 1, 1982 (Mar. 1, 1982).

Frann Bennett etal: Program Death-1 Engagement Upon TCR Activation Has Distinct Eyects on Costimulation and Cytokine-Driven Proliferation: Attenuation of ICOS, IL-4, and IL-21, But Not CD28, IL-7, and IL-15 Responses: Luxenberg: The Journal of Immunology: Jan. 15, 2003; 170 (2): pp. 711-718.

John D. Hansen etal: The B7 family of immunoregulatory receptors: A comparative and evolutionary perspective: 2009, Molecular Immunology 46(3): Jan. 2009: pp. 457-472.

Miguel F. Sanmamed etal: Inducible Expression of B7-H1 (PD-L1) and Its Selective Role in Tumor Site Immune Modulation: Cancer J.: Jul.-Aug. 2014: 20(4): pp. 256-261.

Lifeng Wang etal: Human autoimmune diseases: a comprehensive update: The Association for the Publication of the Journal of Internal Medicine 3692015: Oct. 2015: 278(4): pp. 369-395.

Feng Xu et al: Clinicopathological and prognostic value of programmed death ligand-1 (PD-L1) in renal cell carcinoma: a meta-analysis: Int J Clin Exp Med 8(9): Sep. 15, 2015: pp. 14595-14603.

Zhang, Kang et al. 2015, Medicine 94:e515.

Tacovelli, Nole et al. 2016, Target Oncol. 2016;11:143-148.

E. Stefan, H. Annemarie and P. Andreas Methods 34 (2004) 184-199.

Taiwanese Office Action issued on Jul. 23, 2024 in corresponding Taiwanese Application No. 112146458.

Search Report issued on Jul. 23, 2024 in corresponding Taiwan Application No. 112146458.

* cited by examiner

*Primary Examiner* — Julie Wu
*Assistant Examiner* — Jieun Ham
(74) *Attorney, Agent, or Firm* — LADAS & PARRY LLP

(57) ABSTRACT

The present disclosure relates to an anti-PD-L1 antibody or an antigen-binding fragment thereof, comprising: a heavy chain variable region sequence comprising the three CDRs with the sequences of SEQ ID NOs: 2 to 4, or 6 to 8; and a light chain variable region sequence comprising the three CDRs with the sequences of SEQ ID NOs: 10 to 12, or 14 to 16. The present disclosure also relates to a pharmaceutical composition and a method for detecting expression of PD-L1 in a sample.

20 Claims, 16 Drawing Sheets

Specification includes a Sequence Listing.

Anti-PD-L1 1G8 (Protein: SEQ ID NO:1 ; Nucleotide: SEQ ID NO: 17)

heavy chain sequence cag gtg cag ctt cag gag tca gga cct ggc ctg gca aaa cct tct cag act ctg tcc ctc
Q V Q L Q E S G P G L A K P S Q T L S L acc tgt tct gtc act ggc tac tcc atc acc agt gat tac tgg aac tgg atc cgg aaa ttc
T C S V T G Y S I T S D Y W N W I R K F (SEQ ID NO: 2) HCDR1 cca ggg aat aaa ctt gaa ttc atg gga tat ata agc tac act ggt agc act tac tac aat
P G N K L E F M G Y I S Y T G S T Y Y N (SEQ ID NO: 3) HCDR2 cca tct ctc aaa agt cga atc tcc atc act cga gac aca tcc aag aac cag tat tac ctg
P S L K S R I S I T R D T S K N Q Y Y L cag ttg aat tct gtg act act gag gac aca gcc aca tat tac tgt gcc aga aga ggg gaa
Q L N S V T T E D T A T Y Y C A R R G E tgg tta tcc ccg ttt gct tac tgg ggc caa ggg act ctg gtc act gtc tct gca
W L S P F A Y W G Q G T L V T V S A (SEQ ID NO: 4) HCDR3

FIG. 1A

Anti-PD-L1 3C3 (Protein: SEQ ID NO: 5; Nucleotide: SEQ ID NO: 18)

heavy chain sequence

```
gag gtg cag ctt cag gag tca gga cct ggc ctg aca aaa cct tct cag act ctg tcc ctc
 E   V   Q   L   Q   E   S   G   P   G   L   T   K   P   S   Q   T   L   S   L
acc tgt tct gtc act ggc tac tcc atc acc agt gat tac tgg gac tgg atc cgg aaa ttc
 T   C   S   V   T   G   Y   S   I   T   S   D   Y   W   D   W   I   R   K   F
                     (SEQ ID NO: 6) HCDR1
cca ggg aat aaa ctt gaa tac atg gga tat ata agc tac act ggt agc act tac tac aat
 P   G   N   K   L   E   Y   M   G   Y   I   S   Y   T   G   S   T   Y   Y   N
                                          (SEQ ID NO: 7) HCDR2
cca tct ctc aga agt cga atc tcc atc act cga gac aca tcc aag aac cag tat tac ctg
 P   S   L   R   S   R   I   S   I   T   R   D   T   S   K   N   Q   Y   Y   L
cag ttg agt tct gtg act tct gag gac tca gcc aca tat tac tgt gcc aga aga ggg gga
 Q   L   S   S   V   T   S   E   D   S   A   T   Y   Y   C   A   R   R   G   G
tgg tta tcc ccg ttt gtt tac tgg ggc caa ggg act ctg gtc act gtc tct gca
 W   L   S   P   F   V   Y   W   G   Q   G   T   L   V   T   V   S   A
  (SEQ ID NO: 8) HCDR3
```

FIG. 1B

Anti-PD-L1 1G8 (Protein: SEQ ID NO: 9；Nucleotide: SEQ ID NO: 19)
light chain sequence gac att gtg atg tca cag tct cca tcc tcc cta ggt gtg tca gtt gga gag aag att act
D I V M S Q S P S S L G V S V G E K I T atg agc tgc aag tcc agt cag agc ctt tta tat agt agc aat caa aag aac tcc ttg gcc
M S C K S S Q S L L Y S S N Q K N S L A (SEQ ID NO:10) LCDR1 tgg tac cag cag aaa cca ggg cag tct cct aaa ctg ctg att tac tgg gcg tcc act agg
W Y Q Q K P G Q S P K L L I Y W A S T R (SEQ ID NO:11) LCDR2 gaa tct ggg gtc cct gat cgc ttc aca ggc agt gga tct ggg aca gat ttc act ctc acc
E S G V P D R F T G S G S G T D F T L T atc agc agt gtg aag tct gaa gac ctg gca gtt tat tac tgt cag caa tat tat acc tat
I S S V K S E D L A V Y Y C Q Q Y Y T Y (SEQ ID NO:12) LCDR3 cct ttc acg ttc ggt gct ggg acc aat ctg gag ctg aaa
P F T F G A G T N L E L K

FIG. 2A

Anti-PD-L1 3C3 (Protein: SEQ ID NO: 13 ; Nucleotide: SEQ ID NO: 20)
light chain sequence gac act gtg atg tca cag tct cca tcc tcc cta ggt gtg tca gtt gga gag agg gtt act
D T V M S Q S P S S L G V S V G E R V T ttg acc tgc aag tcc cgt cag agc ctt tta ttt agt agc aat caa aaa aac tcc ttg gcc
L T C K S R Q S L L F S S N Q K N S L A (SEQ ID NO: 14) LCDR1 tgg tac cag cag aaa cca ggg cag tct cct aaa ctg ctg att tac tgg gcg tcc act agg
W Y Q Q K P G Q S P K L L I Y W A S T R (SEQ ID NO: 15) LCDR2 gaa tct ggg gtc cct gat cgc ttc aca ggc agt gga tct ggg aca gat ttc act ctc acc
E S G V P D R F T G S G S G T D F T L T atc agc agt gtg aag tct gaa gac ctg gca gtt tat tac tgt cag caa tat tat acc tat
I S S V K S E D L A V Y Y C Q Q Y Y T Y (SEQ ID NO: 16) LCDR3 cct ttc acg ttc ggt gct ggg acc agt ctg gag ctg aaa
P F T F G A G T S L E L K

FIG. 2B

Anti-PDL1 (3C3) humanization design

| Kabat No. | 1 FR1 22 | CDR1 | 36 FR2 49 | CDR2 |
|---|---|---|---|---|
| MOUSE 3C3 VH (SEQ ID NO: 5) | EVQLQESGPGLTKPSQTLSLTCSVT | GYSITSDYWD | WIRKFPGNKLEYMG | YISYTGSTYYNPSLRS |
| IGHV4-59*01 (SEQ ID NO: 21) | QVQLQESGPGLVKPSETLSLTCTVS | GGSISSYYWS | WIRQPPGKGLEWIG | YIYYSGSTNYNPSLKS |
| HU 3C3 VH (SEQ ID NO: 25) | QVQLQESGPGLVKPSQTLSLTCTVS | GYSITSDYWD | WIRQPPGKGLEWIG | YISYTGSTYYNPSLRS |
| HU 3C3 VHB2 (SEQ ID NO: 27) | EVQLQESGPGLVKPSQTLSLTCTVS | GYSITSDYWD | WIRKPPGKGLEYMG | YISYTGSTYYNPSLRS |
| HU 3C3 VHB1 (SEQ ID NO: 28) | EVQLQESGPGLVKPSQTLSLTCTVS | GYSITSDYWD | WIRQPPGKGLEWMG | YISYTGSTYYNPSLRS |

| Kabat No. | 66 FR3 92 | CDR3 103 | FR4 |
|---|---|---|---|
| MOUSE 3C3 VH (SEQ ID NO: 5) | RISITRDTSKNQYYLQLSSVTSEDSATYYCAR | RGGWLSPFVY | WGQGTLVTVSA |
| IGHV4-59*01 (SEQ ID NO: 21) | RVTISVDTSKNQFSLKLSSVTAADTAVYYCAR | | WGQGTLVTVSS |
| HU 3C3 VH (SEQ ID NO: 25) | RVTISVDTSKNQFSLKLSSVTAADTAVYYCAR | RGGWLSPFVY | WGQGTLVTVSS |
| HU 3C3 VHB2 (SEQ ID NO: 27) | RITISRDTSKNQYSLKLSSVTAADTAVYYCAR | RGGWLSPFVY | WGQGTLVTVSS |
| HU 3C3 VHB1 (SEQ ID NO: 28) | RITISRDTSKNQYSLKLSSVTAADTAVYYCAR | RGGWLSPFVY | WGQGTLVTVSS |

FIG. 7

```
                      FR1                          CDR1              FR2          CDR2
Kabat No.             1                     23            35              49        57
MOUSE 3C3 VL          DTVMSQSPSSLGVSVGERVTLTC KSRQSLLFSSNQKNSLA WYQQKPGQSPKLLIY WASTRES
(SEQ ID NO: 13)
IGKV4-1*01            DIVMTQSPDSLAVSLGERATINC KSSQSVLYSSNNKNYLA WYQQKPGQPPKLLIY WASTRES
(SEQ ID NO: 22)
HU0 3C3 VL            DIVMTQSPDSLAVSLGERATINC KSRQSLLFSSNQKNSLA WYQQKPGQPPKLLIY WASTRES
(SEQ ID NO: 26)

                           FR3                        CDR3       FR4
Kabat No.                                   88          98
MOUSE 3C3 VL          GVPDRFTGSGSGTDFTLTISSVKSEDLAVYYC QQYYTYPFT FGAGTSLELK
(SEQ ID NO: 13)
IGKV4-1*01            GVPDRFSGSGSCTDFTLTISSLQAEDVAVYYC QQYYSTP   FGQGTKLEIK
(SEQ ID NO: 22)
HU0 3C3 VL            GVPDRFSGSGSGTDFTLTISSLQAEDVAVYYC QQYYTYPFT FGQGTKLEIK
(SEQ ID NO: 26)
```

FIG. 7 (Cont.)

Anti-PDL1 (1G8) humanization design

| | FR1 | CDR1 | FR2 | CDR2 |
|---|---|---|---|---|
| Kabat No. | 1 22 | | 36 49 | |
| MOUSE 1G8 VH (SEQ ID NO: 1) | QVQLQESGPGLAKPSQTLSLTCSVT | GYSITSDYWN | WIRKFPGNKLEFMG | YISYTGSTYYNPSLKS |
| IGHV4-59*01 (SEQ ID NO: 21) | QVQLQESGPGLVKPSETLSLTCTVS | GGSISSYYWS | WIRQPPGKGLEWIG | YIYYSGSTNYNPSLKS |
| HU 1G8 VH (SEQ ID NO: 35) | QVQLQESGPGLVKPSQTLSLTCTVS | GYSITSDYWN | WIRQPPGKGLEWIG | YISYTGSTYYNPSLKS |
| HU 1G8 VHB2 (SEQ ID NO: 31) | EVQLQESGPGLVKPSQTLSLTCTVS | GYSITSDYWN | WIRKPPGKGLEYMG | YISYTGSTYYNPSLKS |

| | FR3 | CDR3 | FR4 |
|---|---|---|---|
| Kabat No. | 66 92 | 103 | |
| MOUSE 1G8 VH (SEQ ID NO: 1) | RISITRDTSKNQYYLQLNSVTTEDTATYYCAR | RGEWLSPFAY | WGQGTLVTVSA |
| IGHV4-59*01 (SEQ ID NO: 21) | RVTISVDTSKNQFSLKLSSVTAADTAVYYCAR | | WGQGTLVTVSS |
| HU 1G8 VH (SEQ ID NO: 35) | RVTISVDTSKNQFSLKLSSVTAADTAVYYCAR | RGEWLSPFAY | WGQGTLVTVSS |
| HU 1G8 VHB2 (SEQ ID NO: 31) | RITISRDTSKNQYSLKLSSVTAADTAVYYCAR | RGEWLSPFAY | WGQGTLVTVSS |

FIG. 8

| | FR1 | CDR1 | FR2 | CDR2 |
|---|---|---|---|---|
| Kabat No. | 1 ... 23 | 35 | 49 | 57 |
| MOUSE 1G8 VL (SEQ ID NO: 9) | DIVMSQSPSSLGVSVGEKITMSC | KSSQSLLYSSNQKNSLA | WYQQKPGQSPKLLIY | WASTRES |
| IGKV4-1*01 (SEQ ID NO: 22) | DIVMTQSPDSLAVSLGERATINC | KSSQSVLYSSNNKNYLA | WYQQKPGQPPKLLIY | WASTRES |
| IGKV1-39*01 (SEQ ID NO: 23) | DIQMTQSPSSLSASVGDRVTITC | QASQDISNYLN | WYQQKPGKAPKLLIY | DASNLET |
| IGKV2-29*02 (SEQ ID NO: 24) | DIVMTQTPLSLSVTPGQPASISC | KSSQSLLHSDGKTYLY | WYLQKPGQSPQLLIY | EVSSRFS |
| HU0 1G8 VL (SEQ ID NO: 32) | DIVMTQSPDSLAVSLGERATINC | KSSQSLLYSSNQKNSLA | WYQQKPGQPPKLLIY | WASTRES |
| HU 1G8 VL (SEQ ID NO: 33) | DIQMTQSPSSLSASVGDRVTITC | KSSQSLLYSSNQKNSLA | WYQQKPGKAPKLLIY | WASTRES |
| HU2 1G8 VL (SEQ ID NO: 34) | DIVMTQTPLSLSVTPGQPASISC | KSSQSLLYSSNQKNSLA | WYLQKPGQSPQLLIY | WASTRES |

| | FR3 | CDR3 | FR4 |
|---|---|---|---|
| Kabat No. | 88 | 98 | |
| MOUSE 1G8 VL (SEQ ID NO: 13) | GVPDRFTGSGSGTDFTLTISSVKSEDLAVYYC | QQYYTYPFT | FGAGTNLELK |
| IGKV4-1*01 (SEQ ID NO: 22) | GVPDRFSGSGSGTDFTLTISSLQAEDVAVYYC | QQYYSTP | FGQGTKLEIK |
| IGKV1-39*01 (SEQ ID NO: 23) | GVPSRFSGSGSGTDFTLTISSLQPEDFATYYC | QQYDNLP | FGQGTKLEIK |
| IGKV2-29*02 (SEQ ID NO: 24) | GVPDRFSGSGSGTDFTLKISRVEAEDVGVYYC | QQYSGYPLT | FGQGTKLEIK |
| HU0 1G8 VL (SEQ ID NO: 32) | GVPDRFSGSGSGTDFTLTISSLQAEDVAVYYC | QQYYTYPFT | FGQGTKLEIK |
| HU 1G8 VL (SEQ ID NO: 33) | GVPSRFSGSGSGTDFTLTISSLQPEDFATYYC | QQYYTYPFT | FGQGTKLEIK |
| HU2 1G8 VL (SEQ ID NO: 34) | GVPDRFSGSGSGTDFTLKISRVEAEDVGVYYC | QQYYTYPFT | FGQGTKLEIK |

FIG. 8 (Cont.)

| One site -- Specific binding | MM | HuB2Hu0 | HuB2Hu | HuB2Hu2 |
|---|---|---|---|---|
| Kd | 0.0666 | 0.1084 | 0.0936 | 0.1011 |

| One site -- Specific binding | MM | HuHu0 | HuB2Hu0 | HuHu | HuB2Hu | HuHu2 | HuB2Hu2 |
|---|---|---|---|---|---|---|---|
| Kd(nM) | 0.1917 | 3.993 | 0.2380 | 3.240 | 0.2480 | 9.687 | 0.1088 |

ANTI-HUMAN PD-L1 ANTIBODIES AND THEIR USES

CROSS-REFERENCE TO RELATED APPLICATIONS

The present application claims priority to U.S. Provisional Application 63/428,802, filed on Nov. 30, 2022. The subject matter of this application is incorporated herein by reference in its entirety.

REFERENCE TO SEQUENCE LISTING SUBMITTED VIA EFS-WEB

This application includes an electronically submitted sequence listing in .xml format. The .xml file contains a sequence listing entitled "US14222.xml" created on Nov. 29, 2023 and is 34,000 bytes in size. The sequence listing contained in this .xml file is part of the specification and is hereby incorporated by reference herein in its entirety.

FIELD OF THE INVENTION

The present disclosure relates to novel human antibodies, particularly to human monoclonal antibodies that is specific to PD-L1 with high affinities. Moreover, the disclosure relates to uses of such antibodies in the treatment and diagnosis of human diseases.

BACKGROUND OF THE INVENTION

Protein Programmed Death 1 (PD-1) is an inhibitory member of the CD28 family of receptors also including CD28, CTLA-4, ICOS, and BTLA. PD-1 is expressed on activated B cells, T cells, and myeloid cells (Bennett, Luxenberg et al. 2003, J Immunol 15 Jan. 2003; 170 (2): 711-718). Its ligand, programmed cell death-ligand 1 (PD-L1), is expressed on some tumor cells and by activated B cells and T cells, dendritic cells, macrophages, and fibroblasts cells (Hansen, Du Pasquier et al. 2009, Mol Immunol. 2009 January; 46(3):457-72). PD-L1 binds PD-1 to attenuate cellular immune responses by inducing T-cell apoptosis or exhaustion. Blockade of the PD-1/PD-L1 pathway with monoclonal antibodies (against PD-1 or PD-L1) is a promising therapeutic approach that is being explored in studies of many types of human cancers (Sanmamed and Chen 2014, Cancer J. 2014 July-August; 20(4):256-61). The results of these studies suggest that PD-L1 plays an important role in helping tumors to escape immune systems by facilitating PD-1/PD-L1 pathway activation.

PD-L1 expression has been observed in various solid tumors, including breast cancer, lung cancer, gastric cancer, colorectal cancer, hepatocellular carcinoma, renal cell carcinoma, testicular cancer and papillary thyroid cancer. Moreover, several meta-analyses have shown that PD-L1 overexpression signifies a poor prognosis in many cancer types (Wang, Wang et al. 2015, J Intern Med. 2015 October; 278(4):369-95; Xu, Xu et al. 2015, Int J Clin Exp Med. 2015 Sep. 15; 8(9):14595-603; Zhang, Kang et al. 2015, Medicine 94:e515, Iacovelli, Nole et al. 2016, Target Oncol. 2016; 11:143-148). Therefore, there is a need for better antibodies against PD-L1 for the treatment or diagnosis of diseases or conditions mediated by PD-L1.

SUMMARY OF THE INVENTION

In one aspect, the present disclosure relates to antibodies that is specific to human PD-LI.

Accordingly, the present disclosure provides an antibody of the invention or an antigen-binding fragment thereof comprising a heavy chain variable region including HCDR1, HCDR2, and HCDR3, wherein the HCDR1 sequence is GYSITSDYWN (SEQ ID NO: 2), the HCDR2 sequence is YISYTGSTYYNPSLKS (SEQ ID NO: 3), and the HCDR3 sequence is RGEWLSPFAY (SEQ ID NO: 4); or the HCDR1 sequence is GYSITSDYWD (SEQ ID NO: 6), the HCDR2 sequence is YISYTGSTYYNPSLRS (SEQ ID NO: 7), and the HCDR3 sequence is RGGWLSPFVY (SEQ ID NO: 8);

wherein the HCDR sequences are defined according to the method of Kabat nomenclature.

In accordance with embodiments of the disclosure, the complementarity determining region (CDR) in a heavy chain variable region sequence of an antibody that is specific to human PD-L1 has the sequence of SEQ ID NO: 2, 3, 4, 6, 7 or 8, as shown in FIGS. 1A to 1B.

Accordingly, the present disclosure provides an antibody of the invention or an antigen-binding fragment thereof comprising a light chain variable region including LCDR1, LCDR2 and LCDR3, wherein the LCDR1 sequence is KSSQSLLYSSNQKNSLA (SEQ ID NO: 10), the LCDR2 sequence is WASTRES (SEQ ID NO: 11), and the LCDR3 sequence is QQYYTYPFT (SEQ ID NO: 12); or the LCDR1 sequence is KSRQSLLFSSNOKNSLA (SEQ ID NO: 14), the LCDR2 sequence is WASTRES (SEQ ID NO: 15), and the LCDR3 sequence is QQYYTYPFT (SEQ ID NO: 16);

wherein the LCDR sequences are defined according to method of Kabat nomenclature.

In accordance with some embodiments of the disclosure, the complementarity determining region in a light-chain variable region of an antibody that is specific to human PD-L1 has the sequence of SEQ ID NO: 10, 11, 12, 14, 15 or 16, as shown in FIGS. 2A to 2B.

In another aspect, the present disclosure relates to an antibody that is specific to human PD-L1 or an antigen-binding fragment thereof, comprising a heavy chain variable region having HCDR1, HCDR2, and HCDR3 and a light chain variable region having LCDR1, LCDR2 and LCDR3, wherein the heavy-chain variable region comprising HCDR1 having the sequence of SEQ ID NO: 2, HCDR2 having the sequence of SEQ ID NO: 3, and HCDR3 having the sequence of SEQ ID NO: 4, and the light-chain variable region comprising LCDR1 having the sequence of SEQ ID NO: 10, LCDR2 having the sequence of SEQ ID NO: 11, and LCDR3 having the sequence of SEQ ID NO: 12; or the heavy-chain variable region comprising HCDR1 having the sequence of SEQ ID NO: 6, HCDR2 having the sequence of SEQ ID NO: 7, and HCDR3 having the sequence of SEQ ID NO: 8, and the light-chain variable region comprising LCDR1 having the sequence of SEQ ID NO: 14, LCDR2 having the sequence of SEQ ID NO: 15, and LCDR3 having the sequence of SEQ ID NO: 16.

In some embodiments of the disclosure, the antibody is a chimeric, humanized, composite, or human antibody.

In some embodiments of the disclosure, the antibody is multi-specific.

In some embodiments of the disclosure, the heavy chain variable region of the anti-PD-L1 antibody or the antigen-binding fragment thereof comprises the sequence of SEQ ID NO: 1, or a sequence with at least about 90%, 91%, 92%, 93%, 94%, 95%, 96%, 97%, 98% or 99% homology to the sequence of SEQ ID NO: 1; and the light chain variable region comprises the sequence of SEQ ID NO: 9, or a sequence with at least about 90%, 91%, 92%, 93%, 94%, 95%, 96%, 97%, 98% or 99% homology to the sequence of SEQ ID NO: 9.

In some embodiments of the disclosure, the heavy chain variable region of the anti-PD-L1 antibody or the antigen-binding fragment thereof comprises the sequence of SEQ ID NO: 5, or a sequence with at least about 90%, 91%, 92%, 93%, 94%, 95%, 96%, 97%, 98% or 99% homology to the sequence of SEQ ID NO: 5; and the light chain variable region comprises the sequence of SEQ ID NO: 13, or a sequence with at least about 90%, 91%, 92%, 93%, 94%, 95%, 96%, 97%, 98% or 99% homology to the sequence of SEQ ID NO: 13.

In some embodiments of the disclosure, the heavy chain variable region of the anti-PD-L1 antibody or the antigen-binding fragment thereof comprises the sequence of SEQ ID NO: 25, 27 or 28, or a sequence with at least about 90%, 91%, 92%, 93%, 94%, 95%, 96%, 97%, 98% or 99% homology to the sequence of SEQ ID NO: 25, 27 or 28; and the light chain variable region comprises the sequence of SEQ ID NO: 26, 29 or 30, or a sequence with at least about 90%, 91%, 92%, 93%, 94%, 95%, 96%, 97%, 98% or 99% homology to the sequence of SEQ ID NO: 26, 29 or 30.

In some embodiments of the disclosure, the heavy chain variable region of the anti-PD-L1 antibody or the antigen-binding fragment thereof comprises the sequence of SEQ ID NO: 31 or 35, or a sequence with at least about 90%, 91%, 92%, 93%, 94%, 95%, 96%, 97%, 98% or 99% homology to the sequence of SEQ ID NO: 31 or 35; and the light chain variable region comprises the sequence of SEQ ID NO: 32, 33 or 34, or a sequence with at least about 90%, 91%, 92%, 93%, 94%, 95%, 96%, 97%, 98% or 99% homology to the sequence of SEQ ID NO: 32, 33 or 34.

In some embodiments of the disclosure, the anti-PD-L1 antibody or the antigen-binding fragment thereof is a full antibody, an Fab fragment, an F(ab')2 fragment, or an ScFv fragment.

In some embodiments of the disclosure, the anti-PD-L1 antibody or the antigen-binding fragment thereof is a fully human antibody.

In some embodiments of the disclosure, the anti-PD-L1 antibody or the antigen-binding fragment thereof comprises a heavy chain constant region selected from IgG1, IgG2, or IgG4 isoforms and a light chain constant region selected from K subtype or λ isoform.

In some embodiments of the disclosure, the anti-PD-L1 antibody or the antigen-binding fragment thereof forms part of a bispecific or multi-specific antibody by conjugating with a second specific binding domain for a second target. The second specific binding domain for the second target, for example, may be anti-CD3, anti-ICOS or anti-TIM3, etc.

In some embodiments of the disclosure, the anti-PD-L1 antibody or the antigen-binding fragment thereof is conjugated with a therapeutic agent (payload) to form an antibody-drug conjugate (ADC). In some embodiments, the therapeutic agent or payload may be selected for its ability to modulate a function in the PD-L1-expressing cells or PD-1-expression cells. Such therapeutic agents or payloads, for example, may include DM1, MMAE or MMAF.

In some embodiments of the disclosure, the antibody or the antigen-binding fragment thereof is expressed on a surface of a cell. The cell may be an immune cell. In one embodiment of the disclosure, the immune cell is a T cell.

The present disclosure also provides a vector encoding the antibody or the antigen-binding fragment thereof.

In some embodiments of the disclosure, the vector comprises the sequence of SEQ ID NO: 1, 5, 25, 27, 28, 31, or 35, or a sequence with at least about 90%, 91%, 92%, 93%, 94%, 95%, 96%, 97%, 98% or 99% homology to the sequence of SEQ ID NO: 1, 5, 25, 27, 28, 31, or 35; and/or the light chain variable region comprises the sequence of SEQ ID NO: 9, 13, 26, 29, 30, 32, 33, or 34, or a sequence with at least about 90%, 91%, 92%, 93%, 94%, 95%, 96%, 97%, 98% or 99% homology to the sequence of SEQ ID NO: 9, 13, 26, 29, 30, 32, 33, or 34.

In another aspect, the present disclosure provides a genetically engineered cell expressing the antibody or the antigen-binding fragment thereof or containing the vector. The genetically engineered cell may be an immune cell.

The present disclosure also provides a method for manufacturing the antibody or antigen-binding fragment thereof as disclosed herein, comprising: (a) introducing into a host cell one or more polynucleotides encoding said antibody or antigen-binding fragment; (b) culturing the host cell under conditions favorable to expression of the one or more polynucleotides; and (c) optionally, isolating the antibody or antigen-binding fragment from the host cell and/or a medium in which the host cell is grown.

The present disclosure provides a pharmaceutical composition comprising an effective amount of the antibody or the antigen-binding fragment thereof or the genetically engineered cell or the immune cell and a pharmaceutically acceptable carrier.

In some embodiments of the disclosure, the pharmaceutical composition is for use in inhibiting a PD-L1-mediated signal.

In some embodiments of the disclosure, the pharmaceutical composition is for use in treating a disease mediated by PD-L1.

In some embodiments of the disclosure, the PD-L1 mediated disease may be a cancer. The cancers may include, but are not limited to: lung cancer, breast cancer, prostate cancer, colorectal cancer gastric cancer, hepatocellular carcinoma, renal cell carcinoma, testicular cancer, melanoma, leukemia, or papillary thyroid cancer and other advanced solid tumors.

The present disclosure provides a method for detecting expression of PD-L1, comprising contacting a sample with the anti-PD-L1 antibody or the antigen-binding fragment thereof as described herein.

BRIEF DESCRIPTION OF DRAWINGS

FIGS. 1A to 1B show composite, human heavy chain (FIG. 1A, 1G8; FIG. 1B, 3C3) variable region sequences designed to correspond to that of the mouse anti-human PD-L1 antibody.

FIGS. 2A to 2B show composite, human light chain (FIG. 2A, 1G8; FIG. 2B, 3C3) variable region sequences designed to correspond to that of the mouse anti-human PD-1 antibody.

FIG. 3 illustrates the bindings of anti-PD-L1 antibodies to human PD-L1 using ELISA.

FIG. 7 shows the sequence analysis made for humanization of the VL and VH sequences of hum PD-L1 mAb 3C3 and IMGT. In the first line showing with under the residue numbering according the Kabat scheme, the back mutation sites are shown with underling.

FIG. 8 shows the sequence analysis made for humanization of the VL and VH sequences of hum PD-L1 mAb 1G8 and IMGT. In the first line showing with under the residue numbering according the Kabat scheme, the back mutation sites are shown with underling.

DETAILED DESCRIPTION OF THE INVENTION

Figure 3:
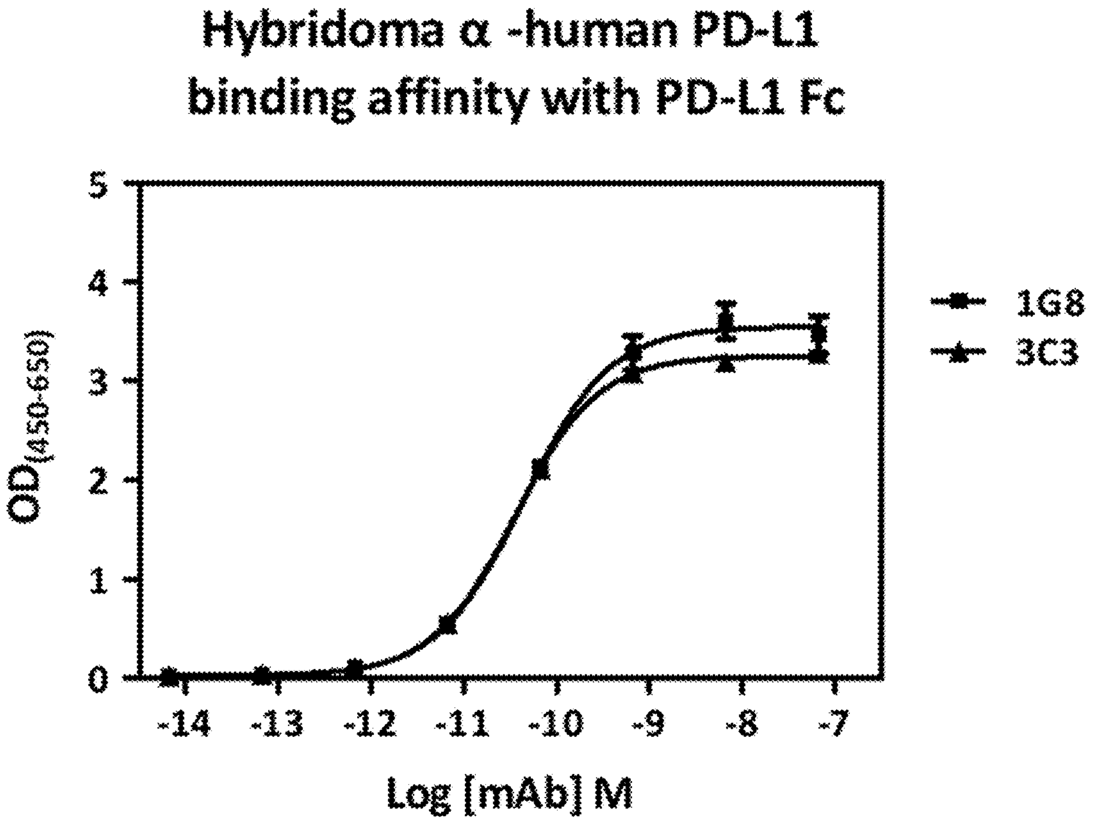

It is understood that this invention is not limited to the particular materials and methods described herein. It is also to be understood that the terminology used herein is for the purpose of describing particular embodiments and is not intended to limit the scope of the present invention, which will be limited only by the appended claims.

It must be noted that, as used in this specification and the appended claims, the singular forms "a," "an," and "the" include plural referents unless the content clearly dictates otherwise.

The term "antibody", as used herein, means any antigen-binding molecule or molecular complex comprising at least one complementarity determining region (CDR) that specifically binds to or interacts with a particular antigen (PD-L1). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-PD-L1 antibody (or antigen-binding portion thereof) may be identical to the human germline sequences, or may be naturally or artificially modified. An amino acid consensus sequence may be defined based on a side-by-side analysis of two or more CDRs.

As used herein, the term "specifically binds" means that an antibody does not cross react to a significant extent with other epitopes.

As used herein, the term "epitope" refers to the site on the antigen to which an antibody binds.

As used herein, the term "complementarity determining region" (CDR) refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

The term "monoclonal antibody" as used herein is not limited to antibodies produced through hybridoma technology. A monoclonal antibody is derived from a single clone, including any eukaryotic, prokaryotic, or phage clone, by any means available or known in the art.

The term "chimeric" antibody as used herein refers to an antibody having variable sequences derived from a non-human immunoglobulin and human immunoglobulin constant regions, typically chosen from a human immunoglobulin template.

"Humanized" forms of non-human antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence.

As used herein, the term "composite antibody" refers to an antibody which has variable regions comprising germline or non-germline immunoglobulin sequences from two or more unrelated variable regions.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex.

As used in the present invention, the term "therapeutic agent" means any compound, substance, drug, drug or active ingredient having a therapeutic or pharmacological effect that is suitable for administration to a mammal, for example a human.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "T cell" includes $CD4^+$ T cells and $CD8^+$ T cells. The term T cell also includes T helper 1 type T cells, T helper 2 type T cells, T helper 17 type T cells and inhibitory T cells.

As used herein, the term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "genetically engineered" or "genetic engineering" of cells means manipulating genes using genetic materials for the change of gene copies and/or gene expression level in the cell. The genetic materials can be in the form of DNA or RNA. The genetic materials can be transferred into cells by various means including viral transduction and non-viral transfection. After being genetically engineered, the expression level of certain genes in the cells can be altered permanently or temporarily.

As used in the present invention, the term "pharmaceutical composition" means a mixture containing a therapeutic agent administered to a mammal, for example a human, for preventing, treating, or eliminating a particular disease or pathological condition that the mammal suffers.

As used herein, the term "therapeutically effective amount" or "efficacious amount" refers to the amount of an antibody that, when administered to a mammal or other subject for treating a disease, is sufficient to effect such treatment for the disease.

As used herein, the terms "treatment," "treating," and the like, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "in need of treatment" refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that includes the knowledge that the subject is ill, or will be ill, as the result of a condition that is treatable by the compounds of the present disclosure.

"Cancer," "tumor," and like terms include precancerous, neoplastic, transformed, and cancerous cells, and can refer to a solid tumor, or a non-solid cancer (see, e.g., Edge et al. AJCC Cancer Staging Manual (7th ed. 2009); Cibas and Ducatman Cytology: Diagnostic principles and clinical correlates (3rd ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, Culture of Animal Cells a Manual of Basic Technique (3rd ed. 1994)). Although transformation can arise from infection with a transforming virus and incorporation of new genomic DNA, or uptake of exogenous DNA, it can also arise spontaneously or following exposure to a carcinogen.

As used herein, the term "sample" encompasses a variety of sample types obtained from an individual, subject or patient and can be used in a diagnostic or monitoring assay. The definition encompasses blood and other liquid samples of biological origin, solid tissue samples such as a biopsy specimen or tissue cultures or cells derived therefrom and the progeny thereof.

The present invention relates to a novel antibody that is specific to and has high affinities for PD-L1. The anti-PD-L1 antibody or an antigen-binding fragment thereof can deliver therapeutic benefits to a subject. The anti-PD-L1 antibody or the antigen-binding fragment thereof according to the disclosure, which may be human or humanized, can be used as therapeutics for treating and/or diagnosing a variety of disorders mediated by PD-L1, which are more fully described herein.

Particularly, the antibody or the antigen-binding fragment thereof according to embodiments of the disclosure is specific to an epitope in human PD-L1 or a fragment thereof.

The antibody or the antigen-binding fragment thereof according to embodiments of the disclosure can be full-length (for example, an IgG1 or IgG4 antibody), or may comprise only an antigen-binding portion (for example, a Fab, F(ab')2, or scFv fragment), and may be modified to affect functionalities as needed.

The antibody or the antigen-binding fragment thereof according to embodiments of the disclosure is specific to human PD-L1. PD-L1, also known as CD274 or B7 homolog 1, is a 40kDa type 1 transmembrane protein that has been speculated to play a major role in suppressing the immune system during particular events, such as pregnancy, tissue allografts, autoimmune disease and other disease states such as hepatitis. Normally, the immune system reacts to foreign antigens that are associated with exogenous or endogenous danger signals, which trigger a proliferation of antigen-specific $CD8^+$ T cells and/or $CD4^+$ helper cells. The binding of PD-L1 to PD-1 or B7.1 transmits an inhibitory signal that reduces the proliferation of these T cells and can also induce apoptosis, which is further mediated by a lower regulation of the gene Bcl-2.

Non-limiting examples of an antigen-binding fragment includes: (i) Fab fragments; (ii) $F(ab')_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody typically comprises at least one variable domain. The variable domain may be of any size or amino acid composition and will generally comprise at least one CDR, which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

As with a full antibody molecule, an antigen-binding fragment may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In one embodiment of the disclosure, the antibody or antigen-binding fragment thereof is conjugated with a therapeutic agent. Antibodies of the disclosure may be used as antibody-drug conjugates (ADCs), which can specifically target PD-L1. The conjugates on the ADCs may modulate the immune cells that express PD-L1 or cells that interact with cells that express PD-L1 (e.g., PD-1 expressing cells). These ADCs can use any antibody of the invention, or an antigen-binding fragment thereof. The drugs (payloads) that are conjugated to the antibody (or binding fragment) can be any that are commonly used in ADCs. The methods for conjugation can be those known in the art.

As applied to polypeptides, the term "homology" means that two peptide sequences, when optimally aligned, such as by the programs GAP or BESTFIT using default gap weights, share at least 95% sequence identity, even more preferably at least 98% or 99% sequence identity. According to embodiments of the invention, the Gap and Best fit program in GCG software was used with default parameters to determine sequence homology or sequence identity between closely related polypeptides.

In embodiments of the disclosure, the anti-PD-L1 antibody or the antigen-binding fragment thereof comprises a heavy chain variable region and a light chain variable region, wherein the heavy chain variable region comprises 3 CDR regions, CDRH1 (or HCDR1), CDRH2 (or HCDR2) and CDRH3 (or HCDR3) regions, and the light chain variable region comprises 3 CDR regions, CDRL1 (or LCDR1), CDRL2 (or LCDR2) and CDRL3 (or LCDR3) regions.

Referring to FIGS. 1A to 2B, in some embodiments of the disclosure, the CDRH1 region comprises the amino acid sequence of SEQ ID NO: 2, the CDRH2 region comprises the amino acid sequence of SEQ ID NO: 3, the CDRH3 region comprises the amino acid sequence of SEQ ID NO: 4, the CDRL1 region comprises the amino acid sequence of SEQ ID NO: 10, the CDRL2 region comprises the amino acid sequence of SEQ ID NO: 11, and the CDRL3 region comprises the amino acid sequence of SEQ ID NO: 12.

In some embodiments of the disclosure, the CDRH1 region comprises the amino acid sequence of SEQ ID NO: 6, the CDRH2 region comprises the amino acid sequence of SEQ ID NO: 7, the CDRH3 region comprises the amino acid sequence of SEQ ID NO: 8, the CDRL1 region comprises the amino acid sequence of SEQ ID NO: 14, the CDRL2 region comprises the amino acid sequence of SEQ ID NO: 15, and the CDRL3 region comprises the amino acid sequence of SEQ ID NO: 16.

In some embodiments of the disclosure, the anti-PD-L1 antibody or the antigen-binding fragment thereof comprises a heavy chain variable region comprising the amino acid sequence of SEQ ID NO: 1 and a light chain variable region comprising the amino acid sequence of SEQ ID NO: 9. In some embodiments of the disclosure, the heavy chain variable region is encoded by the nucleic acid sequence of SEQ ID NO: 17, and the light chain variable region is encoded by the nucleic acid sequence of SEQ ID NO: 19.

In some embodiments of the disclosure, the anti-PD-L1 antibody or the antigen-binding fragment thereof comprises a heavy chain variable region comprising the amino acid sequence of SEQ ID NO: 5 and a light chain variable region comprising the amino acid sequence of SEQ ID NO: 13. In some embodiments of the disclosure, the heavy chain variable region is encoded by the nucleic acid sequence of SEQ ID NO: 18, and the light chain variable region is encoded by the nucleic acid sequence of SEQ ID NO: 20.

The anti-PD-L1 antibody disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes an antibody, and an antigen-binding fragment thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another mammalian germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

In some embodiments of the disclosure, the antibody according to the disclosure is a humanized antibody. In order to improve the binding affinity of the humanized antibody according to the disclosure, some amino acid residues in the human framework region are replaced by the corresponding amino acid residues in the species of CDRs; e.g. a rodent.

In some embodiments of the disclosure, the humanized anti-PD-L1 antibody or the antigen-binding fragment thereof comprises a heavy chain variable region comprising the amino acid sequence of SEQ ID NO: 25, 27, or 28 and a light chain variable region comprising the amino acid sequence of SEQ ID NO: 26, 29 or 30.

In some embodiments of the disclosure, the humanized anti-PD-L1 antibody or the antigen-binding fragment thereof comprises a heavy chain variable region comprising the amino acid sequence of SEQ ID NO: 31 or 35 and a light chain variable region comprising the amino acid sequence of SEQ ID NO: 32, 33 or 34.

The antibodies of the present disclosure may be mono-specific, bi-specific, or multispecific. Multispecific antibodies may be specific for different epitopes of one target polypeptide or may contain antigen-binding domains specific for more than one target polypeptide. The anti-PD-L1 antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present disclosure includes bi-specific antibodies wherein one arm of an immunoglobulin is specific for PD-L1 or a fragment thereof, and the other arm of the immunoglobulin is specific for a second target or is conjugated to a therapeutic agent.

In some embodiments of the disclosure, the antibody or antigen-binding fragment thereof is in a form of chimeric antigen receptor.

The term “chimeric antigen receptor” or alternatively a “CAR” refers to a recombinant polypeptide construct comprising at least an extracellular antigen binding domain, a transmembrane domain and a cytoplasmic signaling domain (also referred to herein as “an intracellular signaling domain”) comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains.

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3.sup.rd ed. 1997)).

An example of a method for manufacturing the antibody or antigen-binding fragment comprises: (a) introducing into a host cell one or more polynucleotides encoding said antibody or antigen-binding fragment; (b) culturing the host cell under conditions favorable to expression of the one or more polynucleotides; and (c) optionally, isolating the antibody or antigen-binding fragment from the host cell and/or a medium in which the host cell is grown.

A vector can be used to introduce a polynucleotides encoding the antibody or antigen-binding fragment of the invention to a host cell. In one embodiment, one type of vector is a “plasmid”, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as “recombinant expression vectors” (or simply, “expression vectors”). In general, expression vectors of utility in recombinant DNA techniques are often in the form of plasmids. In the present specification, “plasmid” and “vector” may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

In another aspect, the present disclosure provides a genetically engineered cell expressing the antibody or antigen-binding fragment thereof or containing the vector. The genetically engineered cell may be an immune cell or a stem cell.

The disclosure provides pharmaceutical compositions comprising the antibody or antigen-binding fragment thereof, genetically engineered cell or immune cell of the present disclosure. The pharmaceutical compositions of the disclosure are formulated with suitable diluents, carriers, excipients, and other agents that provide improved transfer, delivery, tolerance, and the like. The compositions may be formulated for specific uses, such as for veterinary uses or pharmaceutical uses in humans. The form of the composition and the excipients, diluents and/or carriers used will depend upon the intended uses of the antibody and, for therapeutic uses, the mode of administration. A multitude of appropriate formulations can be found in the formulary known to all pharmaceutical chemists: Remington’s Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present disclosure is used for treating a condition or disease associated with PD-L1 in an adult patient, it may be advantageous to intravenously administer the antibody of the present disclosure. Depending on the severity of the condition, the frequency and the duration of the treatment can be adjusted. Effective dosages and schedules for administering the antibody may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

In some embodiments of the disclosure, the pharmaceutical composition is for use in inhibiting a PD-L1-mediated signal.

In some embodiments of the disclosure, the pharmaceutical composition is for use in treating a disease mediated by PD-L1.

The present disclosure provides a method for detecting expression of PD-L1, comprising contacting a sample with the anti-PD-L1 antibody or the antigen-binding fragment thereof as described herein.

The anti-PD-L1 antibody of the present disclosure may also be used to detect and/or measure PD-L1, or PD-L1-expressing cells in a sample, e.g., for diagnostic purposes. For example, an anti-PD-L1 antibody, or fragment thereof, may be used to diagnose a condition or disease characterized by aberrant expression (e.g., over-expression, under-expression, lack of expression, etc.) of PD-L1. Exemplary diagnostic assays for PD-L1 may comprise, e.g., contacting a sample, obtained from a patient, with an anti-PD-L1 antibody of the disclosure, wherein the anti-PD-L1 antibody is labeled with a detectable label or reporter molecule. Alternatively, an unlabeled anti-PD-L1 antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure PD-L1 in a sample include enzyme-linked immunosorbent assay (ELISA), radioimmunoassay (RIA), and fluorescence-activated cell sorting (FACS).

The following examples are provided to aid those skilled in the art in practicing the present disclosure.

EXAMPLES

Antibodies of the disclosure are confirmed to have specific bindings with PD-L1 via ELISA. Briefly, PD-L1 was coated on a 96-well ELISA plate (0.1 μg/well). After binding of anti-PD-L1 antibodies, a goat anti mouse IgG conjugated with horse radish peroxidase (HRP) was used as a second antibody and 3,3',5,5'-Tetramethylbenzidine (TMB) was used as a substrate to assess the antibody-PD-L1 bindings. The OD405 was read to calculate the activities. As shown in the Table 1 and FIG. 3, several mouse hybridoma anti-human PD-L1 antibodies (mAbs 1G8, and 3C3. all show specific and tight bindings with PD-L1.

TABLE 1

ELISA KD of several mouse hybridoma anti-human PD-L1 antibodies

| Clone | Conc. (mg/ml) | Volume (ml) | Endotoxin (EU/mg) | ELISA $K_D$ | Luc repoter $EC_{50}$ (M) |
|---|---|---|---|---|---|
| 1G8 | 4.66 | 5.0 | <5 | $4.35 \times 10^{-11}$ | $6.2 \times 10^{-10}$ |
| 3C3 | 5.42 | 8.5 | <5 | $3.56 \times 10^{-11}$ | $5.8 \times 10^{-10}$ |

Figure 4:
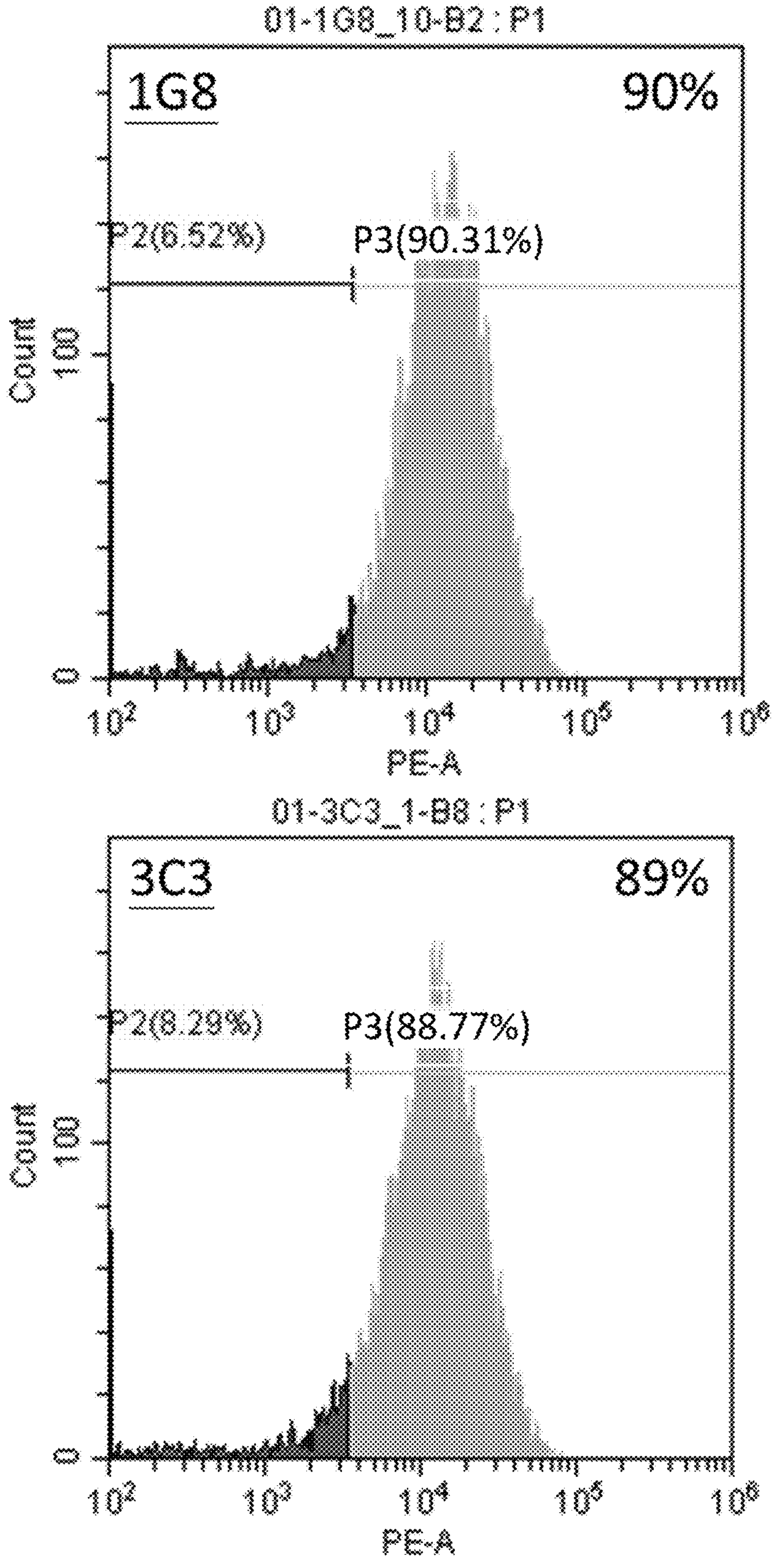
FIG. 4 shows the anti-PD-L1 antibodies binding to HCC827 cells assayed with Flow Cytometry.

To further validate the utility of antibodies of the invention in cancer treatments, the abilities of these antibodies to bind PD-L1 expressed on cancer cells were assessed. For example, binding of anti-PD-L1 antibodies to PD-L1 expressing cells was assayed by Flow Cytometry using HCC827 cells (lung adenocarcinoma), which express high-level PD-L1. Briefly, HCC827 cells (PD-L1 high) were incubated with anit-PD-L1 antibodies for 1 hour, then analyzed using flow cytometry. As shown in FIG. 4, mAbs of the invention 1G8, and 3C3 all can bind HCC827 cells, indicating that these antibodies can recognize PD-L1 on the cancer cell surfaces. Other antibodies of the invention also show similar activities. Therefore, antibodies of the invention can be used to treat cancers by binding to PD-L1 expressed on cancer cells and thereby inhibiting PD-L1 mediated immune suppression or exhaustion.

While the above experiment tests the binding of antibodies of the invention to PD-L1 molecule in vitro, such binding was also tested with PD-1 and PD-L1 respectively expressed on interaction cells. For example, the PD-1/PD-L1 blockage assay may use any commercial kit, such as the kit from Promega (Maddison, WI, USA). The Promega PD-1/PD-L1 Blockade Bioassay is a bioluminescent cell-based assay. The assay kit consists of two genetically engineered cell lines: PD-1 Effector Cells, which are Jurkat T cells expressing human PD-1 and a luciferase reporter driven by an NFAT response element (NFAT-RE), and PD-L1 aAPC/CHO-K1 Cells, which are CHO-K1 cells expressing human PD-L1 and an engineered cell surface protein designed to activate cognate TCRs in an antigen-independent manner.

When the two cell types are co-cultured, the PD-1/PD-L1 interaction inhibits TCR signaling and NFAT-RE-mediated luminescence. Addition of anti-PD-L1 antibodies of the invention that block the PD-1/PD-L1 interactions can release the inhibitory signal, leading to TCR activation and NFAT-RE-mediated luminescence. The bioluminescent signal can be detected and quantified using the Bio-Glo™ Luciferase Assay System and a standard luminometer, such as the GloMax® Discover System from PROMEGA® (Maddison, WI, USA).

Figure 5:
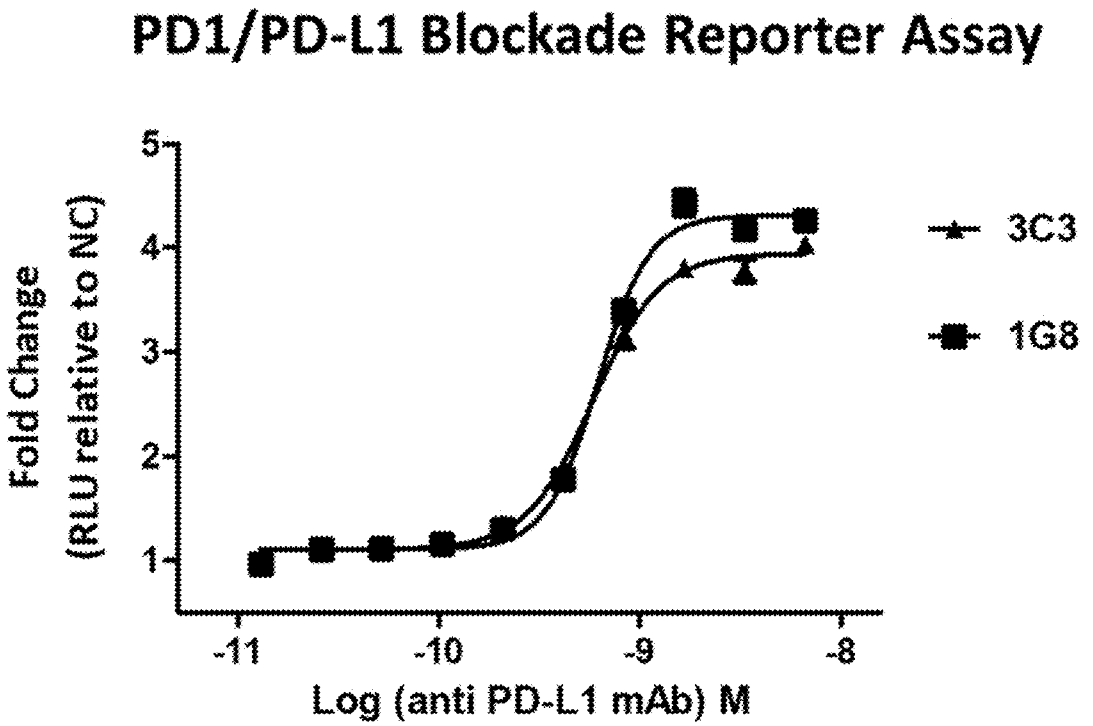
FIG. 5 illustrates the ability of the various antibodies to induce PD-1/PD-L1 blockade.

As shown in the Table 2 and FIG. 5, mAbs of the invention 1G8, and 3C3 all show specific and potent activities that block PD-1/PD-L1 interactions. Other antibodies of the invention also show similar activities. These results confirm that antibodies of the invention would be effective in relieving immune suppression mediated by PD-1 and PD-L1 interactions on interacting cells. Therefore, antibodies of the invention should be useful as therapeutics for diseases arising from immune suppression or exhaustion due to PD-1 and/or PD-L1 signaling. Such diseases include various cancers.

TABLE 2

PD1/PD-L1 Blockade Reporter Assay

| | 3C3 | 1G8 |
|---|---|---|
| $EC_{50}$ | 5.821E−10 | 6.198E−10 |

Some embodiments of the invention relate to methods for treating, or alleviating conditions/symptoms of, a disease mediated by PD-1 and/or PD-L1 signaling; such diseases may include cancers. To demonstrate the utility of antibodies of the invention in treating cancers, a murine syngeneic model was used. Briefly, B-hPD-1/hPD-L1 mice were subcutaneously injected with MC38-hPD-L1 tumor cells ($5\times10^5$) suspended in 0.1 mL PBS in the right front flank for tumor development. Tumor-bearing animals were randomly enrolled into seven study groups when the mean tumor size reached 75±25 $mm^3$. G1 group consists of 6 mice. G2~G7 group consists of 8 mice. The three groups were Mu IgG (5 mg/kg), 3C3 (5 mg/kg), 1G8 (5 mg/kg). All test articles were intraperitoneally administrated to tumor-bearing mice at a frequency of twice per week for total six times. The tumor volume and body weight were measured and recorded twice per week. The study was terminated seven days post last dosing. At the end of this experiment, tumors were removed from euthanized animals, weighed and photographed.

Figure 6:
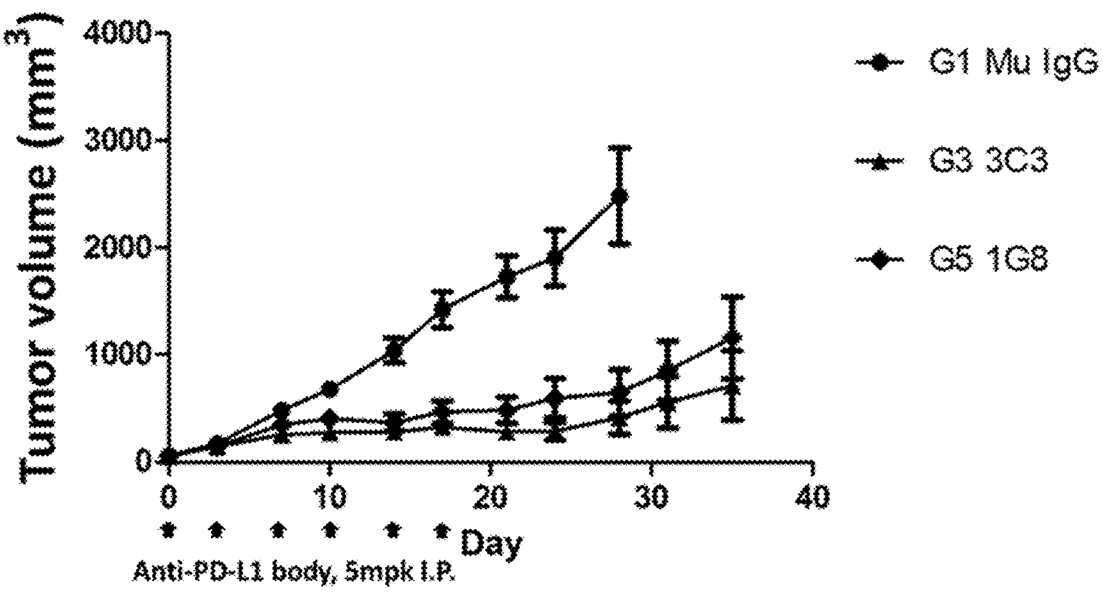
FIG. 6 shows the in vivo efficacy of anti-PD-L1 mAb treatment in the murine syngeneic MC38 colon cancer model.

As shown in the Table 3 and FIG. 6, no unplanned animal death nor obvious clinical sign was found during the study. The body weights of all groups were gradually increased during this study, indicating a good tolerance of animals to test articles. On day 28 post start of treatment, the mean tumor volume of Mu IgG (5 mg/kg) group was 2486±447 $mm^3$. 3C3 (5 mg/kg) treated group, the mean tumor volume was 415±155 $mm^3$ with a TGITV of 85.3%. 1G8 (5 mg/kg) treated group, the mean tumor volume was 647±216 $mm^3$ with a TGITV of 75.8%.

TABLE 3

Efficacy Evaluation of αPD-L1 Abs in the Treatment of the Subcutaneous MC38-hPD-L1 Colon Carcinoma Model in Humanized B-hPD-1/hPD-L1 Mice

| | Mu IgG | 3C3 | 1G8 |
|---|---|---|---|
| $TGI_{28\ day}$(%) | | 85.3 | 75.8 |

In this experiment, 3C3 and 1G8 demonstrated significant anti-tumor activity under the tested dosages and presented no negatively affecting the animal body weight or inducing any obvious clinical sign. These results clearly demonstrate that antibodies of the invention will be useful for clinical uses to treat cancers, such as lung cancer, breast cancer, prostate cancer, colorectal cancer, etc.

Mouse monoclonal antibody may induce potent immunogenicity and anti-drug antibody in patients. Therefore, humanization of mouse monoclonal antibody is an essential and critical step for further drug development. By using 3C3 and 1G8 mouse monoclonal antibodies as the parent antibody, mAb CDR sequences based on the Kabat definitions were described in the FIG. 1 and FIG. 2 (SEQ ID NO: 1 to SEQ ID NO: 20).

For humanized mAb preparation, human germline VL and VH sequences with higher degree of homology with the 3C3 and 1G8 mAb framework regions were identified from the IMGT database (the International immunogenetics Information System®). The homology searches may be performed with sequence BLAST or similar methods. The mouse mAb variable region sequences were used as query sequences. These researches identified the human VH germline gene IGHV4-59*01 (SEQ ID NO: 21) and VL germline gene IGKV4-1*01 (SEQ ID NO: 22), IGKV1-39*01 (SEQ ID NO: 23) and IGKV2-29*01 (SEQ ID NO: 24), respectively, as the VH and VL sequences with more homologous to the corresponding heavy chain and light chain framework sequences in mouse mAb.

Based on the selected human heavy chain and light chain variable region homologs, an anti-PDL1 antibody may be constructed by grafting known CDR sequences from a known anti-PDL1 antibody (e.g., mAb 3C3 and 1G8) into the homologous human heavy chain and light chain variable sequences. As shown in FIG. 7 and FIG. 8, these pairs of light chain and heavy chain sequences are used as examples for the construction of humanized antibodies against human PDL1.

Grafting of CDR onto frameworks resulted in variable domains (VH and VL) from different sources. Such chimeric domains may not have the optimal sequences. Therefore, affinities of the antibodies may not be the best. To improve the binding affinity, some amino acids may be mutated back to the other species. These critical amino acid residues sometimes influence antibody bindings that are located the antibody upper core region and the interface area (E. Stefan, H. Annemarie and P. Andreas Methods 34 (2004) 184-199). In the following additional considerations: (i) to avoid most structurally conserved strands of the Fv b-barrel; (ii) to rank resurfacing site (mouse amino acid) by relative high surface accessibility (e.g., greater than 30%); and (iii) to classify framework generally reported risk sites. According to the principles described above, humanized 3C3 Hu-B1 (VH) and 3C3 Hu-B2 (VH) were designed six and eight back mutation sites on the framework's region, respectively (FIG. 7 and Table 4). Humanized 1G8 Hu-B2 (VH) was designed seven back mutation sites on the framework's region (FIG. 8 and Table 5). The obtained heavy chain of mAb 3C3 is HU 3C3 VH as SEQ ID NO: 25; HU 3C3 VHB2 as SEQ ID NO: 27 and HU 3C3 VHB1 as SEQ ID NO: 28. The obtained light chain of mAb 3C3 is HU0 3C3 VL as SEQ ID NO: 26; HU 3C3 VL as SEQ ID NO: 29 and HU2 3C3 VL as SEQ ID NO: 30. The obtained heavy chain of mAb 1G8 is HU 1G8 VHB2 as SEQ ID NO: 31 and HU 1G8 VH as SEQ ID NO: 35. The obtained light chain of mAb 1G8 is HU0 1G8 VL as SEQ ID NO: 32; HU 1G8 VL as SEQ ID NO: 33 and HU2 1G8 VL as SEQ ID NO: 34.

TABLE 4

Humanized 3C3 frameworks and list of back mutation sites.

| Name | Frame work | Back mutation | Backs |
|---|---|---|---|
| | | 3C3 Heavy chain | |
| M | Mouse | All mouse | |
| Hu | IGH4-59*01F | 16(E16Q) | 1 |
| Hu-B1 | | 1, 16, 48, 67, 71, 78 | 6 |
| Hu-B2 | | 1, 16, 39, 47, 48, 67, 71, 78 | 8 |
| | | 3C3 Light chain | |
| Hu0 | IGKV4-1*01 | No back mutation | 0 |
| Hu | IGKV1-39*01 | No back mutation | 0 |
| Hu2 | IGKV2-29*01 | No back mutation | 0 |

Table 4 shows primary sequence alignments of the framework regions of the VH segments of various anti-PD-L1 (3C3) antibodies: mouse anti-PD-L1 antibodies (M), humanized anti-PD-L1 antibodies (Hu), back mutated humanized anti-PD-L1 antibodies (Hu-B1), further refined anti-PD-L1 antibodies (Hu-B2). Primary sequence alignments of the framework regions of the VL segments of various anti-PD-L1 antibodies: mouse anti-PD-L1 antibodies (M), humanized anti-PD-L1 antibodies (H), no back mutation humanized anti-PD-L1 antibodies (Hu0), further refined anti-PD-L1 antibodies (Hu), and anti-PD-L1 antibodies (Hu2).

TABLE 5

Humanized 1G8 frameworks and list of back mutation sites.

| Name | Frame work | Back mutation | Backs |
|---|---|---|---|
| | | 1G8 Heavy chain | |
| M | Mouse | All mouse | |
| Hu | IGH4-59*01F | 16(E16Q) | 1 |
| Hu-B2 | | 1, 16, 39, 47, 67, 71, 78 | 7 |
| | | 1G8 Light chain | |
| Hu0 | IGKV4-1*01 | No back mutation | 0 |
| Hu | IGKV1-39*01 | No back mutation | 0 |
| Hu2 | IGKV2-29*01 | No back mutation | 0 |

Table 5 shows primary sequence alignments of the framework regions of the VH segments of various anti-PD-L1 (1G8) antibodies: mouse anti-PD-L1 antibodies (M), humanized anti-PD-L1 antibodies (Hu), back mutated humanized anti-PD-L1 antibodies, further refined anti-PD-L1 antibodies (Hu-B2). Primary sequence alignments of the framework regions of the VL segments of various anti-PD-L1 antibodies: mouse anti-PD-L1 antibodies (M), humanized anti-PD-L1 antibodies (H), no back mutation humanized anti-PD-L1 antibodies (Hu0), further refined anti-PD-L1 antibodies (Hu), and anti-PD-L1 antibodies (Hu2).

Figure 9:
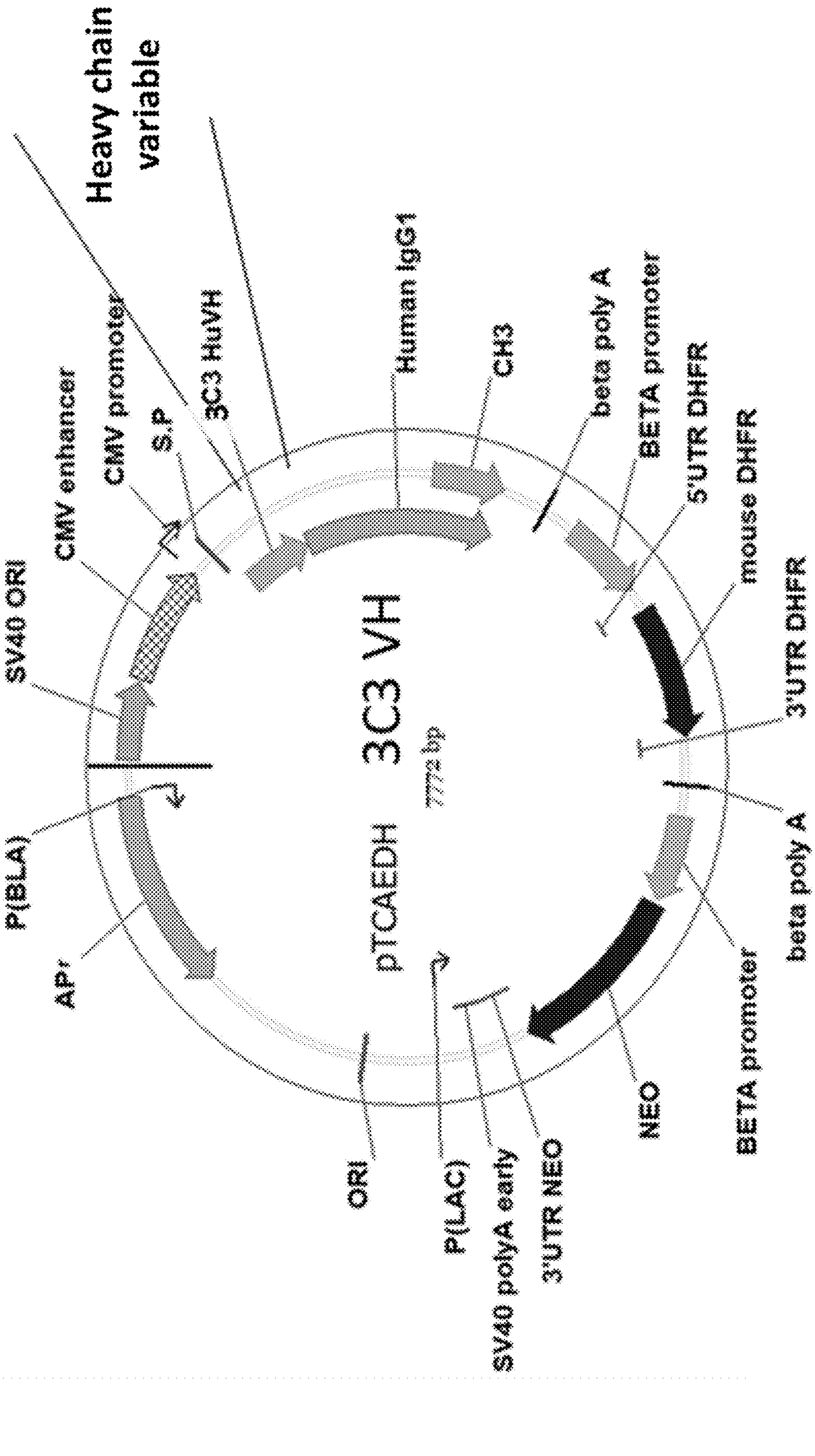
FIG. 9 shows an expression vector for the generation of mouse-human chimera and humanized editions of PD-L1 (3C3) mAb. The detailed procedures for the purification of the different PD-L1 (3C3) mAb editions of antibodies are described in the disclosure.
Figure 9:
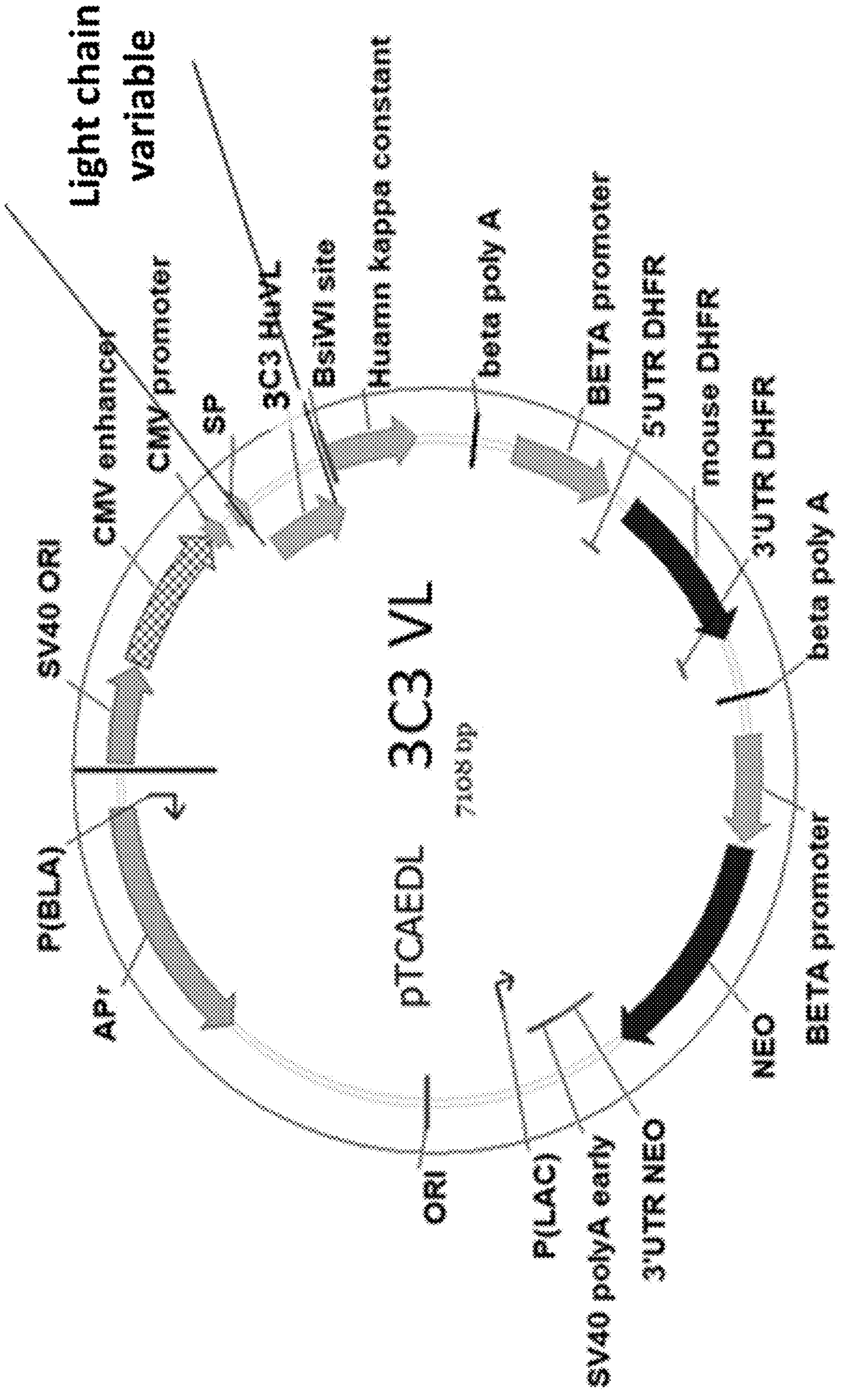
Figure 9:
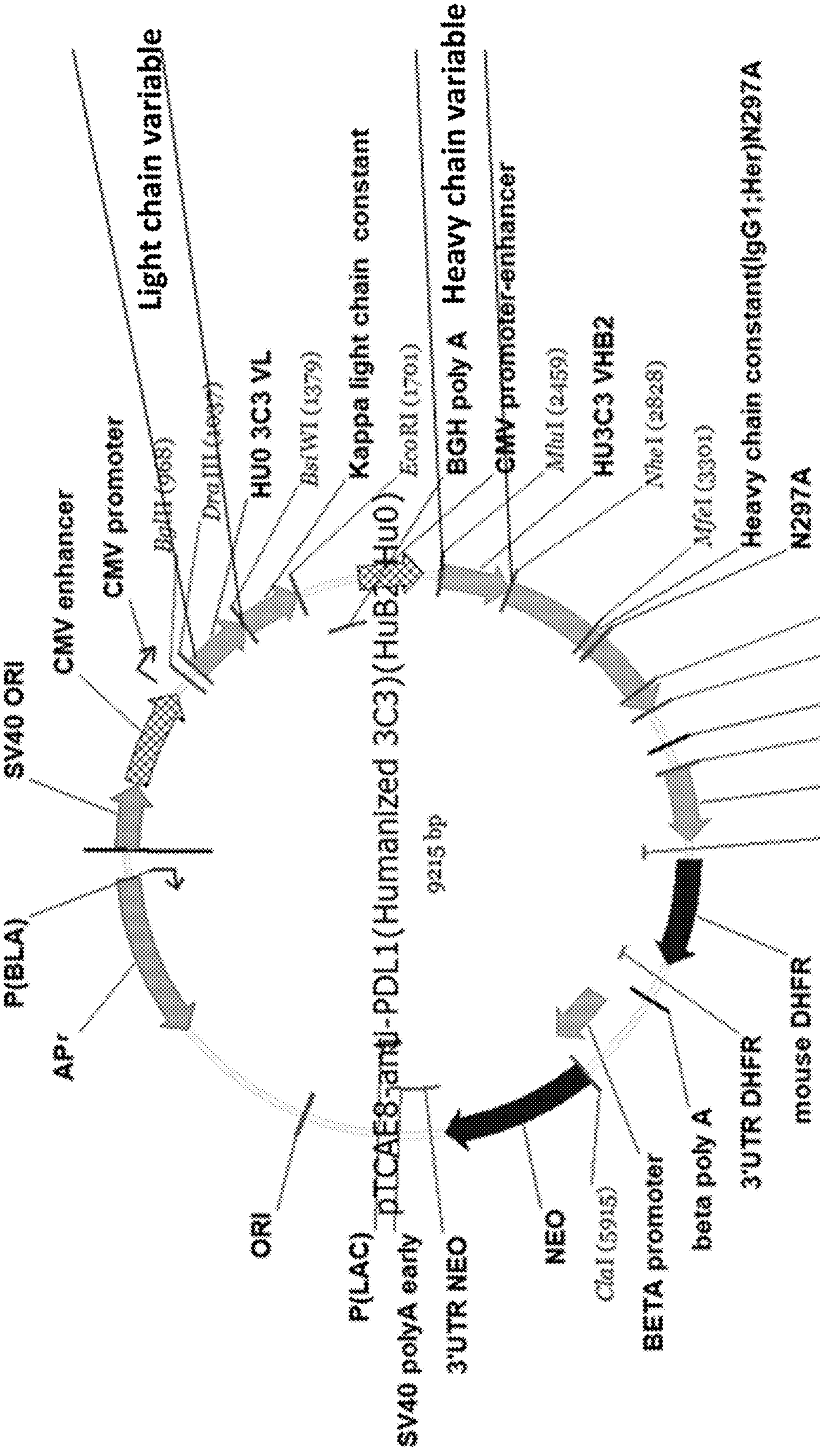

To confirm the affinity change after the mouse antibody was humanized, the variable regions of humanized light chain and humanized heavy chains were directly generated by the nucleotide synthesis method, respectively. The mouse or humanized variable regions were constructed into human chimera antibody expression vector pTCAED heavy and pTCAED light plasmid (FIG. 9), and that were introduced into host cells to prepare recombinant antibody-expressing cells. As the host cells for expression, the FreeStyle™293 or Expi 293 cells (manufactured by INVITROGEN™) were used. The vectors were introduced into the host cells by polyethylimine (PEI) in accordance with the instruction manual (manufactured by INVITROGEN™) about the ratio 1.25 microgram of the antibody expression vector was introduced into $1\times10^6$ cells.

A culture supernatant containing human IgG antibody was prepared by the method described below. The antibody producing cells were acclimated in a Free Style™ 293 Expression Medium (GIBCO™). The cells were cultured in a tissue culture flask, and the culture supernatant was collected when the viable rate of the cells was 90%. The collected supernatant was filtered through 10 micrometer and 0.2 micrometer filters (manufactured by Millipore) to remove contaminants. The culture supernatant containing the antibody was affinity-purified using Protein A (manufactured by MILLIPORE™), PBS as an absorption buffer, and 200 mM glycine buffer (pH 2.5) as an elution buffer. The elution fractions were adjusted to around pH 6.0-7.0 by adding 50mM Tris buffer (pH 9.0). The prepared antibody solution was replaced with PBS using a dialysis membrane (10,000 MW cut, manufactured by SPECTRUM™ Laboratories) and filter-sterilized through a membrane filter (manufactured by MILLIPORE™) having a pore size of 0.22 micrometer to yield the purified antibody. The concentration of the purified antibody was determined by measuring the absorbance at 280 nm and converting the measured value based on 1.45 optimal density equaling 1 mg/ml.

The binding activity of humanized antibodies could be efficiently compared by all combination of heavy chains and light chains using mini scale antibody expression. The concentration of antibodies in culture supernatant was determent by anti-human IgG ELISA. For PDL1 ELISA, plates were coating with PDL1-hFc 1 μg/ml and blocked by 5% milk PBS. Assay antibodies were adjusted to 300 ng/ml, 100 μl/well. Anti-PDL1 signals were measured by secondary goat anti-human Kappa HRP IgG 1:4000 and color developed by TMB substrates (KPL). Optical absorption value was measured at OD450-655 nm by Bio-Rad ELISA reader.

The 3C3 humanized antibodies HuHu0, HuHu and HuHu2 are much lower binding signal for PDL1 (for comparison, mAb 3C3, HuB2Hu0, HuB2Hu and HuB2Hu2 in binding ELISA) (Table 6). However, 3C3-HuB2Hu0, 3C3-HuB2Hu and 3C3-HuB2Hu2 showed similar binding signal to parental mouse clone. In comparison to sequence of 3C3 Hu (VH), those in 3C3 HuB2 (VH) contains eight beneficial mutations in the heavy chain framework regions (FIG. 7). These amino acids are found to have been mutated from the residues in 3C3 Hu (VH) back to the corresponding residues in mouse mAb (i.e., back mutations). These amino acids are all in the heavy chain variable sequence, as shown in FIG. 7. The fact that back mutation produced better binders suggests that these residues in the framework regions contribute indirectly to the binding to PDL1. They probably contribute to the maintenance of proper conformations in the CDR regions.

TABLE 6

Humanized 3C3 expression level and PD-L1 binding test form D6 cultured Freestyle 293 cell sup.

| Expression μg/ml | | Light chain M | Light chain Hu0 | Light chain Hu | Light chain Hu2 |
|---|---|---|---|---|---|
| Heavy chain | M | 2.80 | 4.99 | 1.65 | 3.66 |
| | Hu | 2.46 | 8.61 | 1.02 | 2.31 |
| | Hu-B1 | 6.16 | 15.31 | 9.21 | 16.68 |
| | Hu-B2 | 4.90 | 12.36 | 4.52 | 6.73 |

| 300 ng/ml PDL1 binding OD450-650 nM | | Light chain M | Light chain Hu0 | Light chain Hu | Light chain Hu2 |
|---|---|---|---|---|---|
| Heavy chain | M | 1.524 | 1.577 | 1.851 | 1.548 |
| | Hu | 0.25 | 0.15 | 0.148 | 0.081 |
| | Hu-B1 | 0.61 | 0.539 | 0.455 | 0.349 |
| | Hu-B2 | 1.204 | 1.128 | 1.352 | 1.053 |

Table 6 depicts results from using the chimera PD-L1, and hum PD-L1 mAb 3C3 antibodies to determine binding affinity of PD-L1 mAb. Detailed procedures of chimera antibody expression, purification and Kd analysis were performed as described in the disclosure.

ELISA plates were coating with PDL1-hFc 1 ug/ml and blocked by 5% milk PBS, then add assay antibodies form 45 nM to $2.7\times10^{-3}$ nM dilute (4× fold dilution). Assay will measured by add goat anti-human KAPPA HRP IgG 1:4000 and binding curve and KD was determined by GraphPad Prism software using One site-specific binding for none linear fit methods.

Figure 10:
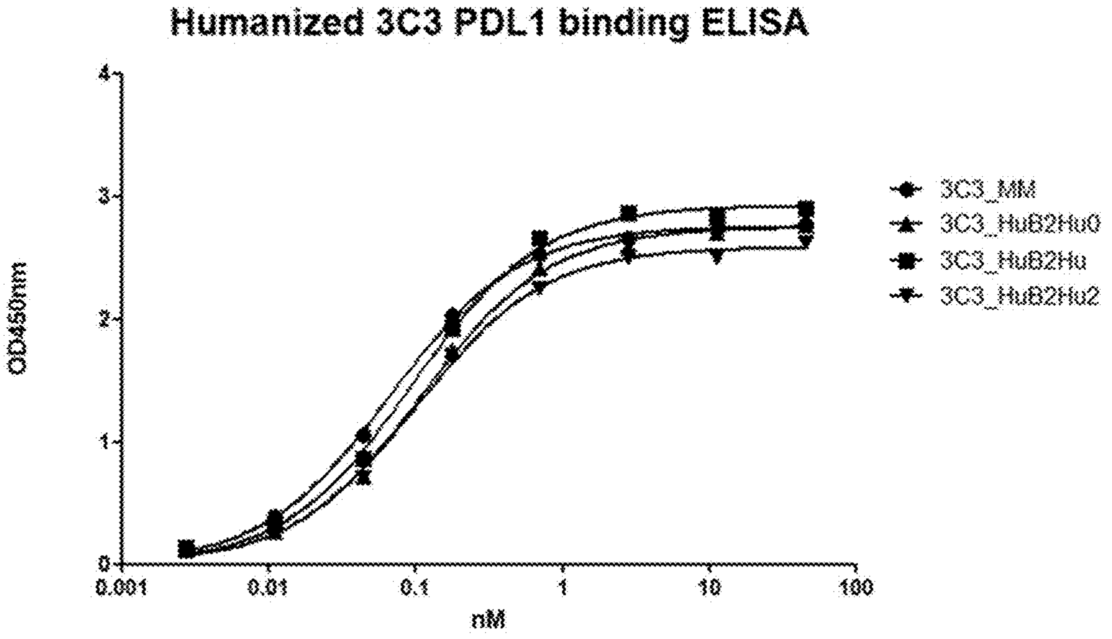
FIG. 10 depicts results from using the mouse-human chimera 3C3 MM and humanized 3C3 HuB2Hu0, 3C3 HuB2Hu, and 3C3 HuB2Hu2 antibodies to determine binding affinity of humanized PD-L1 mAb. Detailed procedures of chimera antibody expression, purification and Kd analysis were performed as described in the disclosure.
Figure 11:
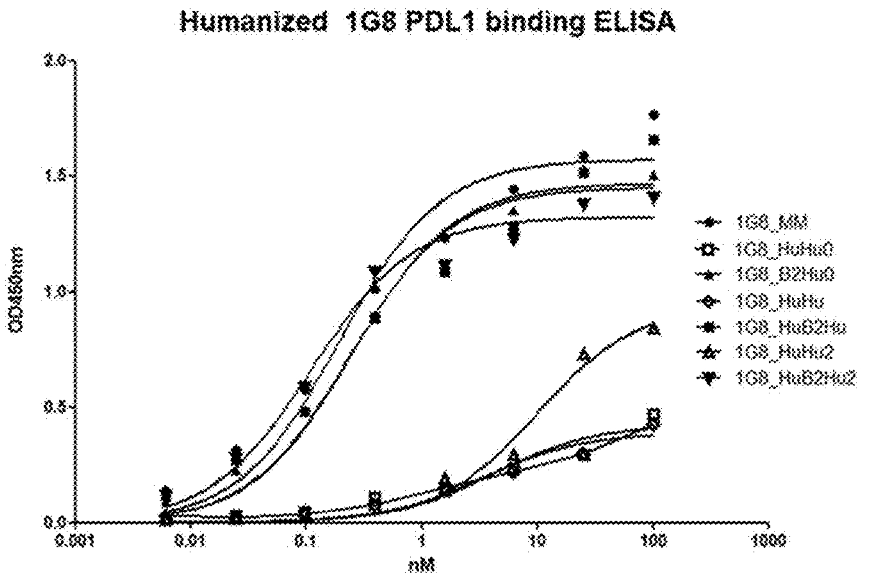
FIG. 11 depicts results from using the mouse-human chimera 1G8 MM and humanized 1G8 HuHu, 1G8 HuB2Hu0, 1G8 HuHu2, 1G8 HuB2Hu, 1G8 HuHu2 and 1G8 HuB2Hu2 antibodies to determine binding affinity of humanized PD-L1 mAb. Detailed procedures of chimera antibody expression, purification and Kd analysis were performed as described in the disclosure.

The binding affinity of 3C3 humanized antibody HuB2Hu0, HuB2Hu and HuB2Hu2 are $1.08\times10^{-10}$ M, $9.36\times10^{-11}$ M, and $1.01\times10^{-10}$ M, respectively. These three humanized antibodies are all shown fewer affinity loss in 2 folds than parental mouse clone 3C3 (FIG. 10). The binding affinity of 1G8 humanized antibodies HuHu0, HuHu and HuHu2 are $3.99\times10^{-9}$ M, $3.24\times10^{-9}$ M and $9.68\times10^{-9}$ M, respectively much lower than mouse clone 1G8. However, the binding affinity of 1G8 humanized antibodies HuB2Hu0, HuB2Hu and HuB2Hu2 are $2.38\times10^{-10}$ M, $2.48\times10^{-10}$ M and $1.08\times10^{-10}$ M, respectively. These humanized 1G8 variants showed similar affinity to parental mouse clone 1G8 (FIG. 11). In comparison to sequence of 1G8 Hu (VH), those in 1G8 HuB2 (VH) contains seven beneficial mutations in the heavy chain framework regions (FIG. 8). The fact that back mutation produced better binders suggests that these residues in the framework regions contribute indirectly to the binding to PDL1.

Figure 12:
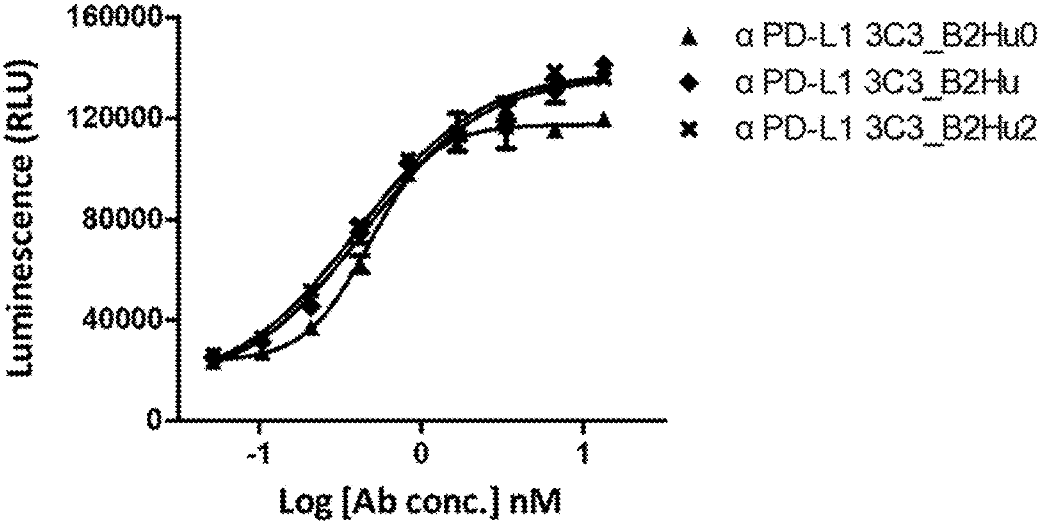
FIG. 12 illustrates the ability of the various humanized PD-L1 3C3 antibodies to induce PD-1/PD-L1 blockade.

As shown in the Table 7 and FIG. 12, mAbs of 3C3 humanized antibody HuB2Hu0, HuB2Hu and HuB2Hu2 all show specific and potent activities that block PD-1/PD-L1 interactions. Other antibodies of the invention also show similar activities. These results confirm that antibodies of the invention would be effective in relieving immune suppression mediated by PD-1 and PD-L1 interactions on interacting cells. Therefore, antibodies of the invention should be useful as therapeutics for diseases arising from immune suppression or exhaustion due to PD-1 and/or PD-L1 signaling. Such diseases include various cancers.

TABLE 7

3C3 humanized antibodies Blockade Reporter Assay

| | αPD-L1 3C3_B2Hu0 | αPD-L1 3C3_B2Hu | αPD-L1 3C3_B2Hu2 |
|---|---|---|---|
| $EC_{50}$ | 4.77E−10 | 4.41E−10 | 4.09E−10 |

Figure 13:
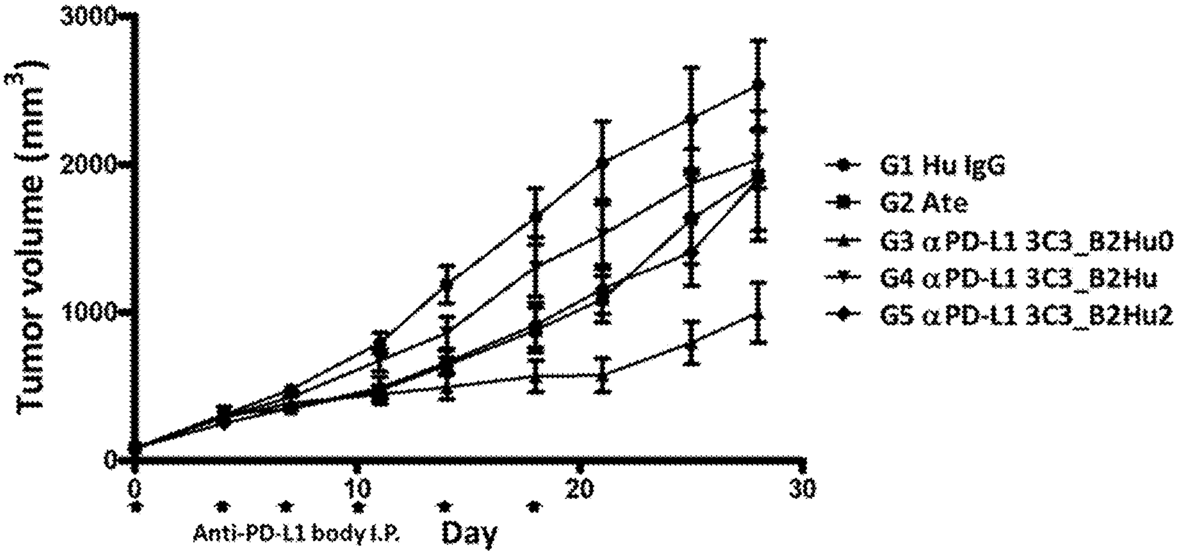
FIG. 13 shows the in vivo efficacy of humanized PD-L1 3C3 antibodies treatment in the murine syngeneic MC38 colon cancer model.

As shown in the Table 8 and FIG. 13, no unplanned animal death nor obvious clinical sign was found during the study. The body weights of all groups were gradually increased during this study, indicating a good tolerance of animals to test articles. At the end of this experiment, the mean tumor volume of IgG group was 2537±300 $mm^3$. In groups of Atezolizumab (Atz), αPD-L1 3C3 B2Hu0, αPD-L1 3C3 B2Hu, and Atz, the mean tumor volume was 1926+436 $mm^3$ with a TGITV of 24.9%, αPD-L1 3C3 B2Hu2, the mean tumor volume was 999±202 $mm^3$ with a TGITV of 62.7%, 2035±191 $mm^3$ with a TGITV of 20.5%, 1900±344 $mm^3$ with a TGITV of 26.0%, respectively. In this experiment, αPD-L1 3C3 B2Hu0 demonstrated significant anti-tumor activity at the level of 5 mg/kg and presented no negatively affecting the animal body weight or inducing any obvious clinical sign.

TABLE 8

Efficacy Evaluation of αPD-L1 Abs in the Treatment of the Subcutaneous

| | Hu IgG | Atz | αPD-L1 3C3_B2Hu0 | αPD-L1 3C3_B2Hu | αPD-L1 3C3_B2Hu2 |
|---|---|---|---|---|---|
| $TGI_{28\ day}$(%) | | 24.9 | 62.7 | 20.5 | 26.0 |

While embodiments of the invention have been illustrated with a limited number of examples, one skilled in the art would appreciate that other modifications and variations are possible. Therefore, the scope of protection of the invention should only be limited by the attached claims.

The invention claimed is:

1. An anti-PD-L1 antibody or an antigen-binding fragment thereof, comprising complementarity determining regions (CDRs) of a heavy chain variable region and complementarity determining regions of a light chain variable region, wherein the heavy-chain variable region comprising HCDR1 having the sequence of SEQ ID NO: 2, HCDR2 having the sequence of SEQ ID NO: 3, and HCDR3 having the sequence of SEQ ID NO: 4, and the light-chain variable region comprising LCDR1 having the sequence of SEQ ID NO: 10, LCDR2 having the sequence of SEQ ID NO: 11, and LCDR3 having the sequence of SEQ ID NO: 12; or the heavy-chain variable region comprising HCDR1 having the sequence of SEQ ID NO: 6, HCDR2 having the sequence of SEQ ID NO: 7, and HCDR3 having the sequence of SEQ ID NO: 8, and the light-chain variable region comprising LCDR1 having the sequence of SEQ ID NO: 14, LCDR2 having the sequence of SEQ ID NO: 15, and LCDR3 having the sequence of SEQ ID NO: 16.

2. The anti-PD-L1 antibody or the antigen-binding fragment thereof according to claim 1, wherein the antibody is a chimeric, humanized, or composite antibody.

3. The anti-PD-L1 antibody or the antigen-binding fragment thereof according to claim 1, wherein the heavy chain variable region comprises the sequence of SEQ ID NO: 1, 5, 25, 27, 28, 31, or 35, or a sequence with at least about 95% homology to the sequence of SEQ ID NO: 1, 5, 25, 27, 28, 31, or 35; and/or the light chain variable region comprises the sequence of SEQ ID NO: 9, 13, 26, 29, 30, 32, 33, or 34, or a sequence with at least about 95% homology to the sequence of SEQ ID NO: 9, 13, 26, 29 or 30, 32, 33, or 34.

4. The anti-PD-L1 antibody or the antigen-binding fragment thereof according to claim 1, wherein the heavy chain variable region comprises the sequence of SEQ ID NO: 1 or a sequence with at least about 95% homology thereto and the light chain variable region comprises the sequence of SEQ ID NO: 9 or a sequence with at least about 95% homology thereto;

the heavy chain variable region comprises the sequence of SEQ ID NO: 5 or a sequence with at least about 95% homology thereto and the light chain variable region comprises the sequence of SEQ ID NO: 13 or a sequence with at least about 95% homology thereto;

the heavy chain variable region comprises the sequence of SEQ ID NO: 25, 27 or 28 or a sequence with at least about 95% homology thereto and the light chain variable region comprises the sequence of SEQ ID NO: 26, 29 or 30 or a sequence with at least about 95% homology thereto; or the heavy chain variable region comprises the sequence of SEQ ID NO: 31 or 35 or a sequence with at least about 95% homology thereto and the light chain variable region comprises the sequence of SEQ ID NO: 32, 33 or 34 or a sequence with at least about 95% homology thereto.

5. The anti-PD-L1 antibody or the antigen-binding fragment thereof according to claim 1, which is conjugated with or covalently linked to a therapeutic agent.

6. The anti-PD-L1 antibody or the antigen-binding fragment thereof according to claim 1, which is linked to a second specific binding domain for a second target.

7. The antibody or the antigen-binding fragment thereof according to claim 1, which is expressed on a surface of a cell.

8. The antibody or the antigen-binding fragment thereof according to claim 7, wherein the cell is an immune cell.

9. The antibody or the antigen-binding fragment thereof according to claim 7, wherein the cell is a T cell.

10. A vector encoding the antibody or antigen-binding fragment thereof according to claim 1.

11. The vector according to claim 10, which comprises the sequence of SEQ ID NO: 1, 5, 25, 27, 28, 31, or 35, or a sequence with at least about 95% homology to the sequence of SEQ ID NO: 1, 5, 25, 27, 28, 31, or 35; and/or the light chain variable region comprises the sequence of SEQ ID NO: 9, 13, 26, 29, 30, 32, 33, or 34, or a sequence with at least about 95% homology to the sequence of SEQ ID NO: 9, 13, 26, 29, 30, 32, 33, or 34.

12. A genetically engineered cell expressing the antibody or the antigen-binding fragment thereof according to claim 1.

13. A genetically engineered cell containing the vector of claim 10.

14. The genetically engineered cell according to claim 13, which is an immune cell.

15. The genetically engineered cell according to claim 13, which is a T cell.

16. A method for manufacturing the antibody or antigen-binding fragment thereof of claim 1, comprising: (a) introducing into a host cell one or more polynucleotides encoding said antibody or antigen-binding fragment; (b) culturing the host cell under conditions favorable to expression of the one or more polynucleotides; and (c) optionally, isolating the antibody or antigen-binding fragment from the host cell and/or a medium in which the host cell is grown.

17. A method for inhibiting a PD-L1-mediated signal in a subject in need thereof, comprising administering the subject with an effective amount of a pharmaceutical composition, wherein the pharmaceutical composition comprises the anti-PD-L1 antibody or the antigen-binding fragment thereof according to claim 1 and a pharmaceutically acceptable carrier.

18. A method for treating a disease mediated by PD-L1 in a subject in need thereof, comprising administering the subject with an effective amount of a pharmaceutical composition, wherein the pharmaceutical composition comprises the anti-PD-L1 antibody or the antigen-binding fragment thereof according to claim 1 and a pharmaceutically acceptable carrier.

19. The method according to claim 18, wherein the disease is a cancer.

20. A method for detecting expression of PD-L1, comprising contacting a sample with the anti-PD-L1 antibody or the antigen-binding fragment thereof according to claim 1.

* * * * *

SEQUENCE LISTING

```
Sequence total quantity: 35
SEQ ID NO: 1            moltype = AA  length = 118
FEATURE                 Location/Qualifiers
source                  1..118
                        mol_type = protein
                        organism = Mus musculus
SEQUENCE: 1
QVQLQESGPG LAKPSQTLSL TCSVTGYSIT SDYWNWIRKF PGNKLEFMGY ISYTGSTYYN  60
PSLKSRISIT RDTSKNQYYL QLNSVTTEDT ATYYCARRGE WLSPFAYWGQ GTLVTVSA    118

SEQ ID NO: 2            moltype = AA  length = 10
FEATURE                 Location/Qualifiers
source                  1..10
                        mol_type = protein
                        organism = Mus musculus
SEQUENCE: 2
GYSITSDYWN                                                         10

SEQ ID NO: 3            moltype = AA  length = 16
FEATURE                 Location/Qualifiers
source                  1..16
                        mol_type = protein
                        organism = Mus musculus
SEQUENCE: 3
YISYTGSTYY NPSLKS                                                  16

SEQ ID NO: 4            moltype = AA  length = 10
FEATURE                 Location/Qualifiers
source                  1..10
                        mol_type = protein
                        organism = Mus musculus
SEQUENCE: 4
RGEWLSPFAY                                                         10

SEQ ID NO: 5            moltype = AA  length = 118
FEATURE                 Location/Qualifiers
source                  1..118
                        mol_type = protein
                        organism = Mus musculus
SEQUENCE: 5
EVQLQESGPG LTKPSQTLSL TCSVTGYSIT SDYWDWIRKF PGNKLEYMGY ISYTGSTYYN  60
PSLRSRISIT RDTSKNQYYL QLSSVTSEDS ATYYCARRGG WLSPFVYWGQ GTLVTVSA    118

SEQ ID NO: 6            moltype = AA  length = 10
FEATURE                 Location/Qualifiers
source                  1..10
                        mol_type = protein
                        organism = Mus musculus
SEQUENCE: 6
GYSITSDYWD                                                         10

SEQ ID NO: 7            moltype = AA  length = 16
FEATURE                 Location/Qualifiers
source                  1..16
                        mol_type = protein
                        organism = Mus musculus
SEQUENCE: 7
YISYTGSTYY NPSLRS                                                  16

SEQ ID NO: 8            moltype = AA  length = 10
FEATURE                 Location/Qualifiers
source                  1..10
                        mol_type = protein
                        organism = Mus musculus
SEQUENCE: 8
RGGWLSPFVY                                                         10

SEQ ID NO: 9            moltype = AA  length = 113
FEATURE                 Location/Qualifiers
source                  1..113
                        mol_type = protein
                        organism = Mus musculus
SEQUENCE: 9
DIVMSQSPSS LGVSVGEKIT MSCKSSQSLL YSSNQKNSLA WYQQKPGQSP KLLIYWASTR  60
ESGVPDRFTG SGSGTDFTLT ISSVKSEDLA VYYCQQYYTY PFTFGAGTNL ELK         113

SEQ ID NO: 10           moltype = AA  length = 17
FEATURE                 Location/Qualifiers
```

```
source                1..17
                      mol_type = protein
                      organism = Mus musculus
SEQUENCE: 10
KSSQSLLYSS NQKNSLA                                               17

SEQ ID NO: 11         moltype = AA  length = 7
FEATURE               Location/Qualifiers
source                1..7
                      mol_type = protein
                      organism = Mus musculus
SEQUENCE: 11
WASTRES                                                          7

SEQ ID NO: 12         moltype = AA  length = 9
FEATURE               Location/Qualifiers
source                1..9
                      mol_type = protein
                      organism = Mus musculus
SEQUENCE: 12
QQYYTYPFT                                                        9

SEQ ID NO: 13         moltype = AA  length = 113
FEATURE               Location/Qualifiers
source                1..113
                      mol_type = protein
                      organism = Mus musculus
SEQUENCE: 13
DTVMSQSPSS LGVSVGERVT LTCKSRQSLL FSSNQKNSLA WYQQKPGQSP KLLIYWASTR  60
ESGVPDRFTG SGSGTDFTLT ISSVKSEDLA VYYCQQYYTY PFTFGAGTSL ELK         113

SEQ ID NO: 14         moltype = AA  length = 17
FEATURE               Location/Qualifiers
source                1..17
                      mol_type = protein
                      organism = Mus musculus
SEQUENCE: 14
KSRQSLLFSS NQKNSLA                                               17

SEQ ID NO: 15         moltype = AA  length = 7
FEATURE               Location/Qualifiers
source                1..7
                      mol_type = protein
                      organism = Mus musculus
SEQUENCE: 15
WASTRES                                                          7

SEQ ID NO: 16         moltype = AA  length = 9
FEATURE               Location/Qualifiers
source                1..9
                      mol_type = protein
                      organism = Mus musculus
SEQUENCE: 16
QQYYTYPFT                                                        9

SEQ ID NO: 17         moltype = DNA  length = 354
FEATURE               Location/Qualifiers
source                1..354
                      mol_type = genomic DNA
                      organism = Mus musculus
SEQUENCE: 17
caggtgcagc ttcaggagtc aggacctggc ctggcaaaac cttctcagac tctgtccctc  60
acctgttctg tcactggcta ctccatcacc agtgattact ggaactggat ccggaaattc  120
ccagggaata aacttgaatt catgggatat ataagctaca ctggtagcac ttactacaat  180
ccatctctca aaagtcgaat ctccatcact cgagacacat ccaagaacca gtattacctg  240
cagttgaatt ctgtgactac tgaggacaca gccacatatt actgtgccag aagaggggaa  300
tggttatccc cgtttgctta ctggggccaa gggactctgg tcactgtctc tgca        354

SEQ ID NO: 18         moltype = DNA  length = 354
FEATURE               Location/Qualifiers
source                1..354
                      mol_type = genomic DNA
                      organism = Mus musculus
SEQUENCE: 18
gaggtgcagc ttcaggagtc aggacctggc ctgacaaaac cttctcagac tctgtccctc  60
acctgttctg tcactggcta ctccatcacc agtgattact gggactggat ccggaaattc  120
ccagggaata aacttgaata catgggatat ataagctaca ctggtagcac ttactacaat  180
ccatctctca gaagtcgaat ctccatcact cgagacacat ccaagaacca gtattacctg  240
cagttgagtt ctgtgacttc tgaggactca gccacatatt actgtgccag aagaggggga  300
```

```
tggttatccc cgtttgttta ctggggccaa gggactctgg tcactgtctc tgca       354

SEQ ID NO: 19          moltype = DNA  length = 339
FEATURE                Location/Qualifiers
source                 1..339
                       mol_type = genomic DNA
                       organism = Mus musculus
SEQUENCE: 19
gacattgtga tgtcacagtc tccatcctcc ctaggtgtgt cagttggaga gaagattact  60
atgagctgca agtccagtca gagcctttta tatagtagca atcaaaagaa ctccttggcc  120
tggtaccagc agaaaccagg gcagtctcct aaactgctga tttactgggc gtccactagg  180
gaatctgggg tccctgatcg cttcacaggc agtggatctg ggacagattt cactctcacc  240
atcagcagtg tgaagtctga agacctggca gtttattact gtcagcaata ttatacctat  300
cctttcacgt tcggtgctgg gaccaatctg gagctgaaa                         339

SEQ ID NO: 20          moltype = DNA  length = 339
FEATURE                Location/Qualifiers
source                 1..339
                       mol_type = genomic DNA
                       organism = Mus musculus
SEQUENCE: 20
gacactgtga tgtcacagtc tccatcctcc ctaggtgtgt cagttggaga gagggttact  60
ttgacctgca agtcccgtca gagcctttta tttagtagca atcaaaaaaa ctccttggcc  120
tggtaccagc agaaaccagg gcagtctcct aaactgctga tttactgggc gtccactagg  180
gaatctgggg tccctgatcg cttcacaggc agtggatctg ggacagattt cactctcacc  240
atcagcagtg tgaagtctga agacctggca gtttattact gtcagcaata ttatacctat  300
cctttcacgt tcggtgctgg gaccagtctg gagctgaaa                         339

SEQ ID NO: 21          moltype = AA  length = 108
FEATURE                Location/Qualifiers
source                 1..108
                       mol_type = protein
                       organism = Homo sapiens
SEQUENCE: 21
QVQLQESGPG LVKPSETLSL TCTVSGGSIS SYYWSWIRQP PGKGLEWIGY IYYSGSTNYN  60
PSLKSRVTIS VDTSKNQFSL KLSSVTAADT AVYYCARWGQ GTLVTVSS               108

SEQ ID NO: 22          moltype = AA  length = 111
FEATURE                Location/Qualifiers
source                 1..111
                       mol_type = protein
                       organism = Homo sapiens
SEQUENCE: 22
DIVMTQSPDS LAVSLGERAT INCKSSQSVL YSSNNKNYLA WYQQKPGQPP KLLIYWASTR  60
ESGVPDRFSG SGSCTDFTLT ISSLQAEDVA VYYCQQYYST PFGQGTKLEI K            111

SEQ ID NO: 23          moltype = AA  length = 105
FEATURE                Location/Qualifiers
source                 1..105
                       mol_type = protein
                       organism = Homo sapiens
SEQUENCE: 23
DIQMTQSPSS LSASVGDRVT ITCQASQDIS NYLNWYQQKP GKAPKLLIYD ASNLETGVPS  60
RFSGSGSGTD FTLTISSLQP EDFATYYCQQ YDNLPFGQGT KLEIK                  105

SEQ ID NO: 24          moltype = AA  length = 112
FEATURE                Location/Qualifiers
source                 1..112
                       mol_type = protein
                       organism = Homo sapiens
SEQUENCE: 24
DIVMTQTPLS LSVTPGQPAS ISCKSSQSLL HSDGKTYLYW YLQKPGQSPQ LLIYEVSSRF  60
SGVPDRFSGS GSGTDFTLKI SRVEAEDVGV YYCQQYSGYP LTFGQGTKLE IK           112

SEQ ID NO: 25          moltype = AA  length = 118
FEATURE                Location/Qualifiers
source                 1..118
                       mol_type = protein
                       organism = synthetic construct
SEQUENCE: 25
QVQLQESGPG LVKPSQTLSL TCTVSGYSIT SDYWDWIRQP PGKGLEWIGY ISYTGSTYYN  60
PSLRSRVTIS VDTSKNQFSL KLSSVTAADT AVYYCARRGG WLSPFVYWGQ GTLVTVSS     118

SEQ ID NO: 26          moltype = AA  length = 113
FEATURE                Location/Qualifiers
source                 1..113
                       mol_type = protein
                       organism = synthetic construct
SEQUENCE: 26
```

```
DIVMTQSPDS LAVSLGERAT INCKSRQSLL FSSNQKNSLA WYQQKPGQPP KLLIYWASTR  60
ESGVPDRFSG SGSGTDFTLT ISSLQAEDVA VYYCQQYYTY PFTFGQGTKL EIK         113

SEQ ID NO: 27          moltype = AA  length = 118
FEATURE                Location/Qualifiers
source                 1..118
                       mol_type = protein
                       organism = synthetic construct
SEQUENCE: 27
EVQLQESGPG LVKPSQTLSL TCTVSGYSIT SDYWDWIRKP PGKGLEYMGY ISYTGSTYYN  60
PSLRSRITIS RDTSKNQYSL KLSSVTAADT AVYYCARRGG WLSPFVYWGQ GTLVTVSS    118

SEQ ID NO: 28          moltype = AA  length = 118
FEATURE                Location/Qualifiers
source                 1..118
                       mol_type = protein
                       organism = synthetic construct
SEQUENCE: 28
EVQLQESGPG LVKPSQTLSL TCTVSGYSIT SDYWDWIRQP PGKGLEWMGY ISYTGSTYYN  60
PSLRSRITIS RDTSKNQYSL KLSSVTAADT AVYYCARRGG WLSPFVYWGQ GTLVTVSS    118

SEQ ID NO: 29          moltype = AA  length = 113
FEATURE                Location/Qualifiers
source                 1..113
                       mol_type = protein
                       organism = synthetic construct
SEQUENCE: 29
DIQMTQSPSS LSASVGDRVT ITCKSRQSLL FSSNQKNSLA WYQQKPGKAP KLLIYWASTR  60
ESGVPSRFSG SGSGTDFTLT ISSLQPEDFA TYYCQQYYTY PFTFGQGTKL EIK         113

SEQ ID NO: 30          moltype = AA  length = 113
FEATURE                Location/Qualifiers
source                 1..113
                       mol_type = protein
                       organism = synthetic construct
SEQUENCE: 30
DIVMTQTPLS LSVTPGQPAS ISCKSRQSLL FSSNQKNSLA WYLQKPGQSP QLLIYWASTR  60
ESGVPDRFSG SGSGTDFTLK ISRVEAEDVG VYYCQQYYTY PFTFGQGTKL EIK         113

SEQ ID NO: 31          moltype = AA  length = 118
FEATURE                Location/Qualifiers
source                 1..118
                       mol_type = protein
                       organism = synthetic construct
SEQUENCE: 31
EVQLQESGPG LVKPSQTLSL TCTVSGYSIT SDYWNWIRKP PGKGLEYMGY ISYTGSTYYN  60
PSLKSRITIS RDTSKNQYSL KLSSVTAADT AVYYCARRGE WLSPFAYWGQ GTLVTVSS    118

SEQ ID NO: 32          moltype = AA  length = 113
FEATURE                Location/Qualifiers
source                 1..113
                       mol_type = protein
                       organism = synthetic construct
SEQUENCE: 32
DIVMTQSPDS LAVSLGERAT INCKSSQSLL YSSNQKNSLA WYQQKPGQPP KLLIYWASTR  60
ESGVPDRFSG SGSGTDFTLT ISSLQAEDVA VYYCQQYYTY PFTFGQGTKL EIK         113

SEQ ID NO: 33          moltype = AA  length = 113
FEATURE                Location/Qualifiers
source                 1..113
                       mol_type = protein
                       organism = synthetic construct
SEQUENCE: 33
DIQMTQSPSS LSASVGDRVT ITCKSSQSLL YSSNQKNSLA WYQQKPGKAP KLLIYWASTR  60
ESGVPSRFSG SGSGTDFTLT ISSLQPEDFA TYYCQQYYTY PFTFGQGTKL EIK         113

SEQ ID NO: 34          moltype = AA  length = 113
FEATURE                Location/Qualifiers
source                 1..113
                       mol_type = protein
                       organism = synthetic construct
SEQUENCE: 34
DIVMTQTPLS LSVTPGQPAS ISCKSSQSLL YSSNQKNSLA WYLQKPGQSP QLLIYWASTR  60
ESGVPDRFSG SGSGTDFTLK ISRVEAEDVG VYYCQQYYTY PFTFGQGTKL EIK         113

SEQ ID NO: 35          moltype = AA  length = 118
FEATURE                Location/Qualifiers
source                 1..118
                       mol_type = protein
```

-continued

```
                    organism = synthetic construct
SEQUENCE: 35
QVQLQESGPG LVKPSQTLSL TCTVSGYSIT SDYWNWIRQP PGKGLEWIGY ISYTGSTYYN  60
PSLKSRVTIS VDTSKNQFSL KLSSVTAADT AVYYCARRGE WLSPFAYWGQ GTLVTVSS    118
```